US007608688B2

(12) United States Patent
Quinnan, Jr. et al.

(10) Patent No.: US 7,608,688 B2
(45) Date of Patent: Oct. 27, 2009

(54) HIV-1 PROTEIN ASSOCIATED WITH BROADLY REACTIVE NEUTRALIZING ANTIBODY RESPONSE

(75) Inventors: Gerald V. Quinnan, Jr., Bethesda, MD (US); Peng Fei Zhang, Bethesda, MD (US)

(73) Assignee: The Henry M. Jackson Foundation for the Advancement of Military Medicine, Inc., Rockville, MD (US)

(*) Notice: Subject to any disclaimer, the term of this patent is extended or adjusted under 35 U.S.C. 154(b) by 94 days.

(21) Appl. No.: 11/473,036

(22) Filed: Jun. 23, 2006

(65) Prior Publication Data

US 2007/0009549 A1 Jan. 11, 2007

Related U.S. Application Data

(62) Division of application No. 09/762,261, filed as application No. PCT/US99/17596 on Aug. 4, 1999, now Pat. No. 7,090,848.

(60) Provisional application No. 60/095,297, filed on Aug. 4, 1998.

(51) Int. Cl.
C07K 14/00 (2006.01)
(52) U.S. Cl. .................................................. 530/350
(58) Field of Classification Search ........................ None
See application file for complete search history.

(56) References Cited

U.S. PATENT DOCUMENTS

| 4,943,627 A | 7/1990 | Gilbert et al. ................ 530/324 |
| 5,019,387 A | 5/1991 | Haynes et al. ................. 424/89 |
| 5,439,809 A | 8/1995 | Haynes et al. ............... 435/69.3 |
| 5,459,060 A | 10/1995 | Cotropia ................... 435/339.1 |
| 5,622,933 A | 4/1997 | Sabatier et al. ................ 514/16 |
| 5,756,674 A | 5/1998 | Katinger et al. ............. 530/350 |
| 5,854,400 A | 12/1998 | Chang et al. ............. 530/378.9 |
| 5,993,819 A | 11/1999 | Haynes et al. ............ 424/188.1 |

FOREIGN PATENT DOCUMENTS

| EP | 0471407 A2 | 2/1992 |
| WO | WO 92/20373 | 11/1992 |
| WO | WO 93/05812 | 4/1993 |

OTHER PUBLICATIONS

Cotropia et al. (1996) A human monoclonal antibody to HIV-1 gp41 with neutralizing activity against diverse laboratory isolates, J. Acquir. Immune Defic. Syndr. Hum. Retrovirol. 12:221-232.
Douglas et al. (1996) An efficient method for the rescue and analysis of functional HIV-1 env genes: evidence for recombination in the vicinity of the tat/rev splice site, AIDS 10:39-46.
Hioe et al. (1997) Neutralization of HIV-1 primary isolates by polyclonal and monoclonal human antibodies, Int. Immunol. 9:1281-1290.
Kelleher et al. (1997) AIDS Research and Human Retroviruses 13(1): 29-32.
Klein et al. (2002) Clinical Therapeutics 22(3): 295-314.
Korber et al. (2001) British Medical Bulletin 58: 19-42.
Lukashov et al. (1996) AIDS Research and Human Retroviruses 12(10): 951-953.
Moore et al. (1993) Probing the structure of the V2 domain of human immunodeficiency virus type 1 surface glycoprotein gp120 with a panel of eight monoclonal antibodies: Human immune response to the V1 and V2 domains, J. Virol. 67:6136-6151.
Muster et al. (1993) A conserved neutralization epitope on gp41 of human immunodeficiency virus type 1, J. Virol. 67:6642-6647.
Purtscher et al. (1994) A broadly neutralizing human monoclonal antibody against gp41 of human immunodeficiency virus type 1, AIDS Res. Hum. Retroviruses 10:1651-1658.
Sabri et al. (1996) Lack of correlation between V3 amino acid sequence and syncytium-inducing capacity of some HIV type 1 isolates, AIDS Res. Hum. Retroviruses, 12:855.
Sala et al. (1994). Journal of Virology. 68 (8): 5280-5283.
Sequence alignment of SEQ ID No. 1 with Lukashov et. al. SPTREMBL_17 datatbase; Accession No. Q69692; 1996 from AIDS Research and Human Retroviruses; 12: 951-953.
Sequence alignment of SEQ ID No. 24 with SPTREMBL database accession No. Q71538 submitted Nov. 1, by Strunnikova et al.
Sequence alignment of SEQ ID No. 1 with Sala et al. SPTREMBL_17; Accession No. Q78039; Nov. 1996; from J. Virol. 68: 5280-5283.
Sequence alignment of SEQ ID No. 24 with geneseq database accession No. AAR77770, submitted Sep. 1995 in WO 94/229339-A1.
Sequence alignment of the V3 region of SEQ ID No. 1 to Geneseq data accession No. AAR20883, submitted Jun. 1, 1992 in EP471407-A of Lewis et al.
Thali et al. (1993) Characterization of conserved human immunodeficiency virus type-1 gp120 neutralization epitopes exposed upon gp120-CD4, J. Virol. 67:3978-3988.
Thali et al. (1994) Resistance to neutralization by broadly reactive antibodies to the human immunodeficiency virus type-1 gp120 glycoprotein conferred by a gp41 amino acid change, J. Virol. 68:674-680.
Trkola et al. (1995) Cross-clade neutralization of primary isolates of human immunodeficiency virus type 1 by human monoclonal antibodies and tetrameric CD4-IgG, J. Virol. 69:6609-6617.
Trkola et al. (1996) Human monoclonal antibody 2G12 defines a distinctive neutralization epitope of human immunodeficiency virus type-1, J. Virol. 70:1100-1108.
VanCott et al. (1997) Antibodies with specificity to native gp120 and neutralization activity against primary human immunodeficiency virus type-1 isolates elicited by immunization with oligomeric gp160, J. Virol. 71:4319-4330.

(Continued)

Primary Examiner—Gary B Nickol
Assistant Examiner—Nicole Kinsey White
(74) Attorney, Agent, or Firm—Morgan, Lewis & Bockius LLP

(57) ABSTRACT

The present invention relates to HIV-1 envelope proteins from a donor with non-progressive HIV-1 infection whose serum contains broadly cross-reactive, primary virus neutralizing antibody. The invention also relates to isolated or purified proteins and protein fragments that share certain amino acids at particular positions with the foregoing HIV-1 proteins.

27 Claims, 4 Drawing Sheets

OTHER PUBLICATIONS

XP002220280, EBI database accession No. O71260, Database EMBL Online, (1998).

XP002220281, EBI database accession No. P88523, Database EMBL Online, (1997).

XP002220282, EBI database accession No. Q73297, Database EMBL Online, (1996).

Zwart et al. (1991) Immunodominance and antigenic variation of the principal neutralization domain of HIV-1, J. Virol. 181:481-489.

Akerblom et al. (1990) Neutralizing cross-reactive and non-neutralizing monoclonal antibodies to HIV-1 gp120, AIDS 4: 953-60 (Abstract Only).

MacGregor et al. (1998) First human trial of a DNA-based vaccine for treatment of human immunodeficiency virus type 1 infection: safety and host response, J. Infect. Dis. 178: 92-100 (Abstract Only).

Nakamura et al. (1992) Monoclonal Antibodies to the extracellular domain of HIV-1 IIIB gp160 that neutralize infectivity, block binding to CD4, and react with diverse isolates, AIDS Res Hum Retroviruses 8: 1875-85 (Abstract Only).

Wagner et al. (1992) Immunological reactivity of human immunodeficiency virus type I derived peptide representing a consensus sequence of the gp120 major neutralizing region V3, Arch. Virol. 127: 139-52 (Abstract only).

FIG. 2

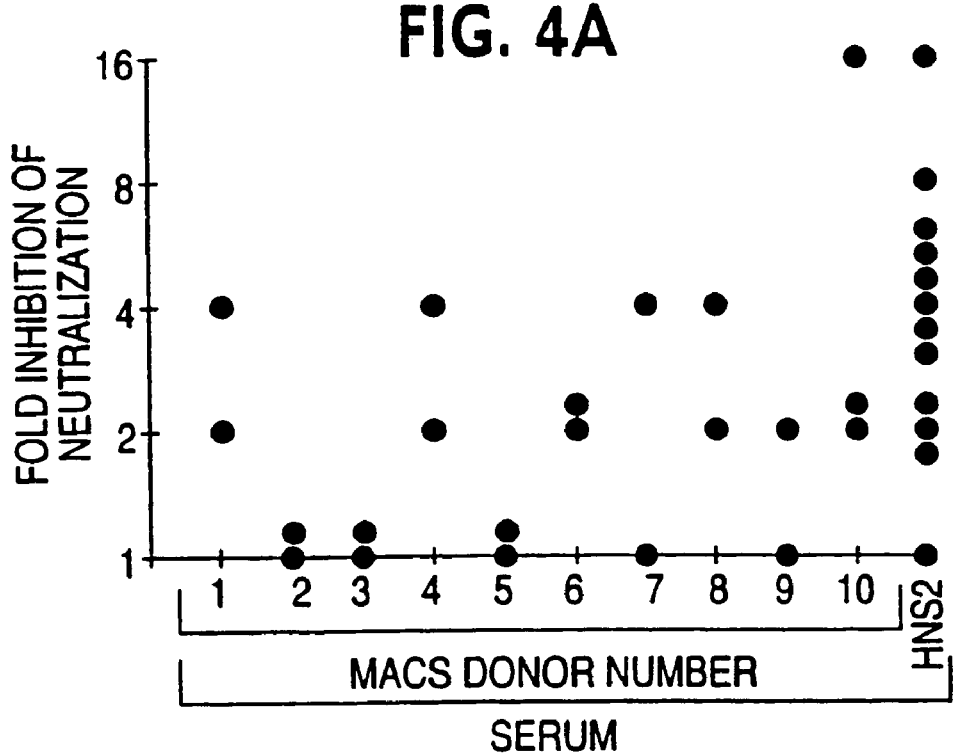
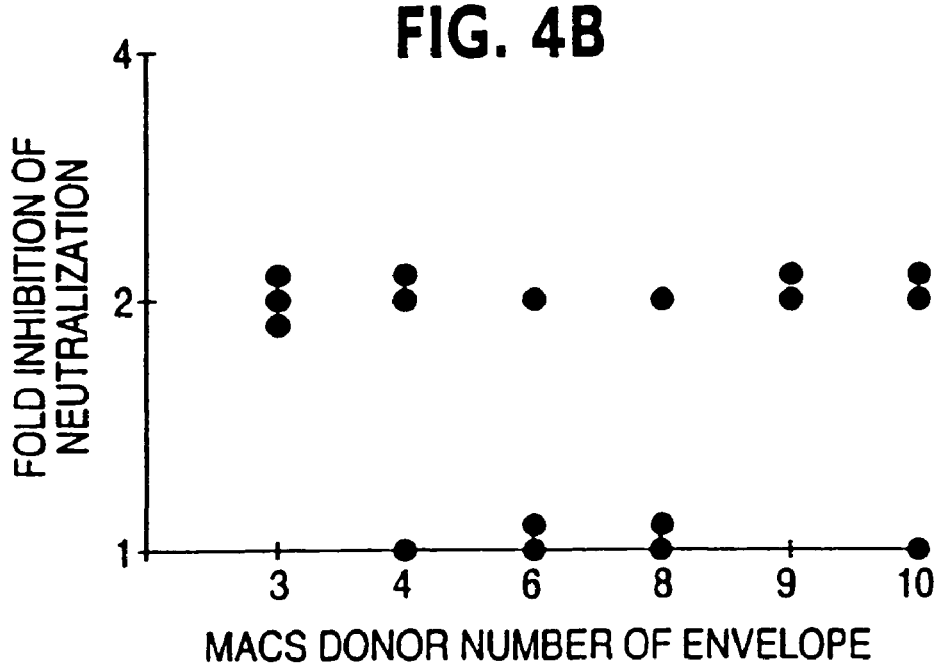

HIV-1 PROTEIN ASSOCIATED WITH BROADLY REACTIVE NEUTRALIZING ANTIBODY RESPONSE

RELATED APPLICATIONS

The present application is a divisional of U.S. patent application Ser. No. 09/762,261 (filed May 29, 2001, now U.S. Pat. No. 7,090,848, issued Aug. 15, 2006, which is a U.S. National Phase Application of International Application PCT/US99/17596 (filed on Aug. 4, 1999), which claims the benefit of U.S. Provisional Application 60/095,267 (filed Aug. 4, 1998), all of which are herein incorporated by reference in their entirety.

ACKNOWLEDGMENT OF FEDERAL SUPPORT

The present invention arose in part from research funded by the following federal grant monies: NIH A137436 and A144339, and USUHS R087E2

TECHNICAL FIELD

The present invention relates to HIV-1 envelope proteins and peptides derived from the donor of the Neutralizing Reference Human Serum (2) which is noted for its capacity to neutralize primary HIV isolates of varied subtypes.

BACKGROUND OF THE INVENTION

The development of a successful vaccine against HIV infection or a vaccine agent capable of preventing HIV disease progression has been a public health goal for over 15 years. One of the immune responses that may be required to elicit a protective immune response against HIV infection is the generation of antibodies that are virus neutralizing.

The target of HIV-1 neutralizing antibodies (NA) is the envelope glycoprotein complex. This complex is a multimeric structure composed of three or four copies each of the gp120 surface and gp41 transmembrane glycoproteins (Luciw, 1996). There are a number of neutralization domains on each of the three or four heterodimeric components of the complex (Thali et al., 1992, 1993; Zwart et al., 1991; Moore et al., 1993; Trkola et al., 1996; Muster et al., 1993; Cotropia et al., 1996; Sabri et al., 1996). The amino acid compositions of the proteins vary substantially from strain to strain. Some of the neutralization domains are in regions which tend to vary greatly, while others are in regions which tend to be highly conserved. The variable neutralization domains include those in variable (V) regions 1, 2, and 3 of gp120, while the conserved domains include the primary receptor binding site, and other epitopes in gp120 and gp41. Amino acid sequence variation is undoubtedly the explanation for the variation that is seen in specificity of neutralization sensitivity among virus strains. However, it has not been possible to classify antigenic subtypes of HIV-1 based on genetic analyses, and various regions of the envelope complex even outside of the neutralization domains have been shown to contribute to antigenic variability (Thali et al., 1994; Back et al., 1993).

Recent findings indicate that the neutralization of primary isolates of HIV may be mediated primarily by antibodies directed against non-V3 region epitopes expressed on the oligomeric complex but not on monomeric gp120, while laboratory adapted strains are more readily neutralized by antibodies directed against V3 (Hioe et al., 1997; VanCott et al., 1997). The identity of the non-V3 epitopes recognized on primary isolates is not established. The presence of antibodies which have broadly neutralizing activity against primary isolates of many subtypes of HIV-1 in sera from infected people is unusual, but the nature of the envelope proteins in individuals with such antibodies may be of interest for defining the epitopes which may be broadly immunogenic in vaccines.

SUMMARY OF THE INVENTION

The present inventors have cloned and characterized the envelope genes from the donor of human serum which is noted for its capacity to neutralize primary HIV isolates of various subtype (Vujcic, et al. 1995, D'Souza et al., 1991).

The invention includes an isolated HIV envelope protein or fragment thereof which, when injected into a mammal, induces the production of broadly cross-reactive neutralizing anti-serum against multiple strains of HIV-1.

The invention further includes an isolated HIV envelope protein or fragment thereof comprising a proline at a position corresponding to amino acid residue 313, a methionine at a position corresponding to amino acid residue 314 and a glutamine at a position corresponding to amino acid residue 325 of SEQ ID NO:1.

In another embodiment, the invention includes an isolated HIV envelope glycoprotein or fragment thereof comprising an alanine at a position corresponding to amino acid residue 167 of SEQ ID NO:1.

The invention also includes an isolated HIV envelope protein comprising the amino acid sequence of SEQ ID NO:1 as well as an isolated nucleic acid molecule encoding the envelope protein, which was deposited with the American Type Culture Collection (ATCC) under accession No. PTA-7237 on Dec. 1, 2005 in accordance with the Budapest Treaty.

Compositions for eliciting an immune response, such as vaccines, immunogenic compositions and attenuated viral vaccine delivery vectors comprising the envelope proteins, peptides and nucleic acids encoding such proteins and peptides of the invention are also included. Methods for generating antibodies in a mammal comprising administering one or more of these proteins, peptides and nucleic acids, in an amount sufficient to induce the production of the antibodies, is also included in the invention.

The invention also comprises a diagnostic reagent comprising one or more of the isolated HIV-1 envelope proteins and methods for detecting broadly cross-reactive neutralizing anti-serum against multiple strains of HIV-1.

BRIEF DESCRIPTION OF THE DRAWINGS

FIG. 2: Neutralization of clade B viruses and pseudoviruses by sera from 10 male residents of the Baltimore/Washington, D.C. area collected from 1985-1990 in the Multicenter AIDS Cohort Study. The P9 and P10 viruses (P9-V and P10-V) are primary isolates from two of the serum donors (Quinnan et al., 1998). The neutralization assays were performed in PM1 cells, as described in the Examples. Each point represents the results obtained with an individual serum. The open bars represent the standard deviations about the geometric means, indicated by the midlines. The numbers above the results obtained using pseudoviruses indicate the probabilities obtained from testing the null hypothesis by paired t testing comparing the individual pseudoviruses to R2.

FIG. 3 (B): Comparative inhibitory effects of peptides on neutralization of R2 and MN (clone V5) pseudoviruses. All peptides were tested at 15 µg/ml. The linear peptides (L) corresponded to the apical sequences of the respective V3 loops. The cyclic peptides (C) corresponded to the full lengths of the respective V3 regions of the different strains. Neutralization in the absence of peptide (None), is also shown.

FIG. 4 (A): Effect of cyclic R2 V3 peptide on neutralization of pseudoviruses. Fold inhibition of neutralization was calculated as the ratio of the 50% neutralization titer obtained in the absence of peptide compared to that obtained in the presence of cyclic R2 V3 peptide (15 µg/ml). All assays were performed in triplicate. Neutralization titers were calculated at the midpoints of the infectivity inhibition curves, since the curves tended to be most parallel in this region. Similar results were obtained comparing 90% neutralization endpoints. Peptide inhibition of neutralization of R2 pseudovirus by sera from MACS donors (donor numbers 1-10), two assays each, and by Reference 2. Results are shown for two determinations for each serum from the MACS donors and for 12 assays of Reference 2 performed during the same time intervals as the other experiments shown in panels (A) and (B).

FIG. 4 (B): Peptide inhibition of neutralization of pseudoviruses expressing MACS patient envelopes (patient numbers 3, 4, 6, 8, 9, and 10) by Reference 2. Results of two or three separate assays of each pseudovirus are shown.

MODES OF CARRYING OUT THE INVENTION

General Description

Figure 1:
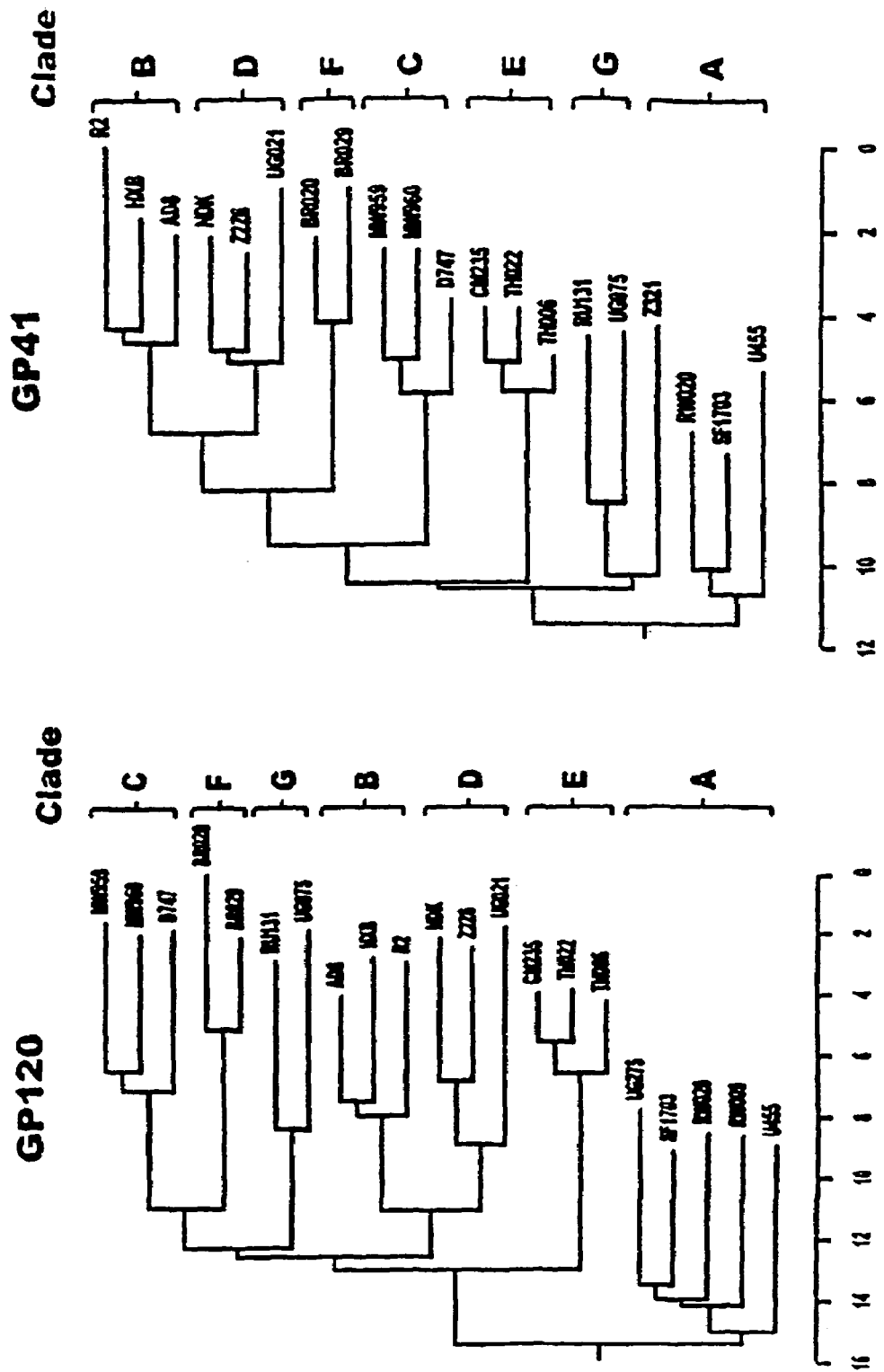
FIG. 1: Phylogenetic analysis of the gp120 and gp41 nucleotide coding sequences of clone R2. Alignments were performed using the Clustial algorithm of Higgins and Sharp in the program DNA Star (Higgins et al., 1989; Saitou et al., 1987; Myers et al., 1988). The graphs at the bottom of the two figures indicate the percent similarity distances represented by the dendograms. Gene bank accession numbers for the sequences represented are: MW 959, U08453; MW960, U08454; D747, X65638; BR020, U27401; BR029, U27413; RU131, U30312; UG975, U27426; AD8, M60472; HXB, K03455; NDK, M27323; Z2Z6, M22639; UG021, U27399; CM235, L03698; TH022, U09139; TH006, U08810; UG275, L22951; SF1703, M66533; RW020, U08794; RW009, U08793; U455, M62320; and Z321, M15896.

A goal of immunization against HIV is to induce neutralizing antibody (NA) responses broadly reactive against diverse strains of virus. The present inventors have studied envelope protein from a donor with non-progressive HIV-1 infection whose serum contains broadly cross-reactive, primary virus NA. DNA was extracted from lymphocytes, which had been collected approximately six and twelve months prior to the time of collection of the cross reactive serum, env genes were synthesized by nested PCR, cloned, expressed on pseudoviruses, and phenotyped in NA assays. Two clones from each time point had identical V3 region nucleotide sequences, utilized CCR5 but not CXCR4 for cell entry, and had similar reactivities with two reference sera. Analysis of the full nucleotide sequence of one clone demonstrated it to be subtype B, with a predicted GPGRAF apical V3 sequence, normal predicted glycosylation, and an intact reading frame.

Infectivity assays of R2 pseudovirus in HOS cells expressing CD4 and various coreceptors demonstrated the envelope to be CCR5 dependent. R2 pseudovirus was compared to others expressing env genes of various clades for neutralization by sera from donors in the United States (presumed or known subtype B infections), and from individuals infected with subtypes A, C, and E viruses. Neutralization by the sera from donors in the United States of pseudoviruses expressing R2 and other clade B envs was similarly low to moderate, although R2 was uniquely neutralized by all. R2 was neutralized by sera from people infected with clades A-F, while other clade B, D, E and G pseudoviruses were neutralized less often. One highly sensitive clade C pseudovirus was neutralized by all the sera, although the titers varied more than 250-fold. The results suggest that the epitope(s) which induced the cross-clade reactive NA in Donor 2 may be expressed on the R2 envelope.

The present invention relates to HIV-1 envelope proteins from this donor who had non-progressive HIV-1 infection whose serum contains broadly cross-reactive, primary virus neutralizing antibody. The invention also relates to isolated or purified proteins and protein fragments that share certain amino acids at particular positions with the foregoing HIV-1 proteins.

SPECIFIC EMBODIMENTS

Proteins and Peptides

Proteins and peptides of the invention include the full length envelope protein having the amino acid sequence of Table 3 (SEQ ID NO:1), gp120 having the amino acid sequence corresponding to gp120 in Table 3 (amino acids: 1-520 of SEQ ID NO:1), gp41 having the amino acid sequence corresponding to gp41 in Table 3 (amino acids 521-866 of SEQ ID NO:1), as well as polypeptides and peptides corresponding to the V3 domain and other domains such as V1/V2, C3, V4, C4 and V5. These domains correspond to the following amino acid residues of SEQ ID NO:1:

| DOMAIN | AMINO ACID RESIDUES |
|--------|---------------------|
| C1     | 30-124              |
| V1     | 125-162             |
| V2     | 163-201             |
| C2     | 202-300             |
| V3     | 301-336             |
| C3     | 337-387             |
| V4     | 388-424             |
| C4     | 425-465             |
| V5     | 466-509             |
| C5     | 510-520             |

Polypeptides and peptides comprising any single domain may be of variable length but include the amino acid residues of Table 3 (SEQ ID NO:1) which differ from previously sequenced envelope proteins. For instance, peptides of the invention which include all or part of the V3 domain may comprise the sequence: PM $X_1$ $X_2$ $X_3$ $X_4$ $X_5$ $X_6$ $X_7$ $X_8$ $X_9$ $X_{10}$Q (SEQ ID NO:5), wherein $X_1$-$X_{10}$ are any natural or non-natural amino acids (P refers to Proline, M refers to methionine and Q refers to Glutamine). Non-natural amino acids include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sat), ornithine (Orn), citrulline (Cit), t-butylalanine (t-BuA), t-butylglycine (t-BuG), N-methylisoleucine (N-Melle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); beta-2-thienylalanine (Thi); and methionine sulfoxide (MSO). Preferably, peptides of the invention are 60%, 70%, 80% or more preferably, 90% identical to the V3 region of the HIV envelope protein of Table 3 (SEQ ID NO:1). Accordingly, V3 peptides of the invention comprise about 13 amino acids but may be 14, 15, 17, 20, 25, 30, 35, 36, 39, 40, 45, 50 or more amino acids in length. In one embodiment, a V3 peptide of 13 amino acids in length consists of the sequence PMGPGRAFYTTGQ (amino acids 313-325 of Table 3 (SEQ ID NO:1).

In another embodiment of the invention, polypeptides and peptides comprising all or part of the V1/V2 domain comprise an amino acid sequence with an alanine residue at a position corresponding to amino acid 167 Table 3 (SEQ ID NO:1). For instance, peptides of the invention spanning the V1/V2 domain may comprise the sequence FNIATSIG (residues 164-171 of SEQ ID NO:1) and may be about 8, 9, 10, 15, 20, 25, 30, 35, 40, 45, 50 or more amino acids in length. As used herein, "at a position corresponding to" refers to amino acid positions in HIV envelope proteins or peptides of the invention which are equivalent to a given amino acid residue in the sequence of Table 1 (SEQ ID NO:1) in the context of the surrounding residues.

The peptides of the present invention may be prepared by any known techniques. Conveniently, the peptides may be prepared using the solid-phase synthetic technique initially described by Merrifield (1965), which is incorporated herein by reference. Other peptide synthesis techniques may be found, for example, in Bodanszky et al., *Peptide Synthesis*, 2d ed. (New York, Wiley, 1976).

Nucleic acids and Recombinant Expression of Peptide or Proteins

Proteins and peptides of the invention may be prepared by any available means, including recombinant expression of the desired protein or peptide in eukaryotic or prokaryotic host cells (see U.S. Pat. No. 5,696,238). Methods for producing proteins or peptides of the invention for purification may employ conventional molecular biology, microbiology, and recombinant DNA techniques within the ordinary skill level of the art. Such techniques are explained fully in the literature. See, for example, Maniatis et al., *Molecular Cloning: A Laboratory Manual*, 2d ed. (Cold Spring Harbor, Cold Spring Harbor Laboratory Press, 1989); Glover, *DNA Cloning: A Practical Approach*, Vols. 1-4 (Oxford, IRL Press, 1985); Gait, *Oligonucleotide Synthesis: A Practical Approach* (Oxford, IRL Press, 1984); Hames & Higgins, *Nucleic Acid Hybridisation: A Practical Approach* (Oxford, IRL Press, 1985); Freshney, *Animal Cell Culture. A Practical Approach* (Oxford, IRL Press, 1992); Perbal, *A Practical Guide To Molecular Cloning* (New York, Wiley, 1984).

The present invention further provides nucleic acid molecules that encode the proteins or peptides of the invention. Such nucleic acid molecules can be in an isolated form, or can be operably linked to expression control elements or vector sequences. The present invention further provides host cells that contain the vectors via transformation, transfection, electroporation or any other art recognized means of introducing a nucleic acid into a cell.

As used herein, a "cell line" is a clone of a primary cell that is capable of stable growth in vitro for many generations.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A polyadenylation signal and transcription termination sequence will usually be located 3' to the coding sequence.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "naked DNA" means nucleic acid molecules that are free from viral particles, particularly retroviral particles. This term also means nucleic acid molecules which are free from facilitator agents including but not limited to the group comprising: lipids, liposomes, extracellular matrix-active enzymes, saponins, lectins, estrogenic compounds and steroidal hormones, hydroxylated lower alkyls, dimethyl sulfoxide (DMSO) and urea.

As used herein, a "nucleic acid molecule" refers to the polymeric form of deoxyribonucleotides (adenine, guanine, thymine, and/or cytosine) in either its single stranded form, or in double-stranded helix as well as RNA. This term refers only to the primary and secondary structure of the molecule and is not limited to any particular tertiary form. In discussing the structure of particular double-stranded DNA molecules, sequences may be described herein according to the normal convention of giving only the sequence in the 5' to 3' direction along the nontranscribed strand of DNA (e.g., the strand having a sequence homologous to the mRNA). Transcriptional and translational control sequences are DNA regulatory sequences, such as promoters, enhancers, polyadenylation signals, terminators, and the like, that provide for the expression of a coding sequence in a host cell.

As used herein, a "promoter sequence" is a DNA regulatory region capable of binding RNA polymerase in a cell and initiating transcription of a downstream (3' direction) coding sequence. For purposes of defining the present invention, the promoter sequence is bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

As used herein, a "replicon" is any genetic element (e.g., plasmid, chromosome, virus) that functions as an autonomous unit of DNA replication in vivo; i.e., capable of replication under its own control.

A "signal sequence" can be included before the coding sequence or the native 29 amino acid signal sequence from the envelope protein of Table 3 may be used. This sequence encodes a signal peptide, N-terminal to the polypeptide, that communicates to the host cell to direct the polypeptide to the cell surface or secrete the polypeptide into the media. This signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, and EP 0116201). Further, the alpha-factor and its analogs have been found to secrete heterologous proteins from a variety of yeast, such as *Saccharomyces* and *Kluyveromyces*, (EP 88312306.9; EP 0324274 publication, and EP 0301669). An example for use in mammalian cells is the tPA signal used for expressing Factor VIIIc light chain.

As used herein, DNA sequences are "substantially homologous" when at least about 85% (preferably at least about 90% and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See, for example, Maniatis et al., supra.

A cell has been "transformed" by exogenous or heterologous DNA when such DNA as been introduced inside the cell. The transforming DNA may or may not be integrated (covalently linked) into chromosomal DNA making up the genome of the cell. In prokaryotes, for example, the transforming DNA may be maintained on an episomal element such as a plasmid or viral vector. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A coding sequence is "under the control" of transcriptional and translational control sequences in a cell when RNA polymerase transcribes the coding sequence into mRNA, which is then translated into the protein encoded by the coding sequence.

As used herein, a "vector" is a replicon, such as plasmid, phage or cosmid, to which another DNA segment may be attached so as to bring about the replication of the attached segment.

Vectors are used to simplify manipulation of the DNA which encodes the HIV proteins or peptides, either for preparation of large quantities of DNA for further processing (cloning vectors) or for expression of the HIV proteins of peptides (expression vectors). Vectors comprise plasmids, viruses (including phage), and integrated DNA fragments, i.e., fragments that are integrated into the host genome by recombination. Cloning vectors need not contain expression control sequences. However, control sequences in an expression vector include transcriptional and translational control sequences such as a transcriptional promoter, a sequence encoding suitable ribosome binding sites, and sequences which control termination of transcription and translation. The expression vector should preferably include a selection gene to facilitate the stable expression of HIV gene and/or to identify transformants. However, the selection gene for maintaining expression can be supplied by a separate vector in cotransformation systems using eukaryotic host cells.

Suitable vectors generally will contain replicon (origins of replication, for use in non-integrative vectors) and control sequences which are derived from species compatible with the intended expression host. By the term "replicable" vector as used herein, it is intended to encompass vectors containing such replicons as well as vectors which are replicated by integration into the host genome. Transformed host cells are cells which have been transformed or transfected with vectors containing HIV peptide or protein encoding DNA. The expressed HIV proteins or peptides may be secreted into the culture supernatant, under the control of suitable processing signals in the expressed peptide, e.g. homologous or heterologous signal sequences.

Expression vectors for host cells ordinarily include an origin of replication, a promoter located upstream from the HIV protein or peptide coding sequence, together with a ribosome binding site, a polyadenylation site, and a transcriptional termination sequence. Those of ordinary skill will appreciate that certain of these sequences are not required for expression in certain hosts. An expression vector for use with microbes need only contain an origin of replication recognized by the host, a promoter which will function in the host, and a selection gene.

Commonly used promoters are derived from polyoma, bovine papilloma virus, CMV (cytomegalovirus, either murine or human), Rouse sarcoma virus, adenovirus, and simian virus 40 (SV40). Other control sequences (e.g., terminator, polyA, enhancer, or amplification sequences) can also be used.

An expression vector is constructed so that the HIV protein or peptide coding sequence is located in the vector with the appropriate regulatory sequences, the positioning and orientation of the coding sequence with respect to the control sequences being such that the coding sequence is transcribed and translated under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. If the selected host cell is a mammalian cell, the control sequences can be heterologous or homologous to the HIV coding sequence, and the coding sequence can either be genomic DNA containing introns or cDNA.

Higher eukaryotic cell cultures may be used to express the proteins of the present invention, whether from vertebrate or invertebrate cells, including insects, and the procedures of propagation thereof are known. See, for example, Kruse & Patterson, *Tissue Culture* (New York, Academic Press, 1973).

Suitable host cells for expressing HIV proteins or peptides in higher eukaryotes include: monkey kidney CVI line transformed by SV40 (COS-7, ATCC CRL1651); baby hamster kidney cells (BHK, ATCC CRL10); Chinese hamster ovary-cells-DHFR (Urlaub & Chasin, 1980); mouse Sertoli cells (Mather, 1980); monkey kidney cells (CVI ATCC CCL70); African green monkey kidney cells (VER076, ATCC CRL1587); human cervical carcinoma cells (HeLa, ATCC CCL2); canine kidney cells (MDCK, ATCC CCL34); buffalo rat liver cells (BRL3A, ATCC CRL1442); human lung cells (W138, ATCC CCL75); human liver cells (HepG2, HB8065); mouse mammary tumor (MMT 060652, ATCC CCL51); rat hepatoma cells (Baumann et al., 1980) and TR1 cells (Mather et al., 1982).

It will be appreciated that when expressed in mammalian tissue, the recombinant HIV gene products may have higher molecular weights than expected due to glycosylation. It is therefore intended that partially or completely glycosylated forms of HIV preproteins or peptides having molecular weights somewhat different from 160, 120 or 41 kD are within the scope of this invention.

Other preferred expression vectors are those for use in eukaryotic systems. An exemplary eukaryotic expression system is that employing vaccinia virus, which is well-known in the art. See, for example, Macket et al. (1984); Glover, supra; and WO 86/07593. Yeast expression vectors are known in the art. See, for example, U.S. Pat. Nos. 4,446,235; 4,443,539; 4,430,428; and EP 103409; EP 100561; EP 96491.

Another preferred expression system is vector pHSI, which transforms Chinese hamster ovary cells (see WO 87/02062). Mammalian tissue may be cotransformed with DNA encoding a selectable marker such as dihydrofolate reductase (DHFR) or thymidine kinase and DNA encoding the HIV protein or peptide. If wild type DHFR gene is employed, it is preferable to select a host cell which is deficient in DHFR, thus permitting the use of the DHFR coding sequence as marker for successful transfection in hgt medium, which lacks hypoxanthine, glycine, and thymidine. An appropriate host cell in this case is the Chinese hamster ovary (CHO) cell line deficient in DHFR activity, prepared and propagated as described by Urlaub & Chasin, (1980).

Depending on the expression system and host selected, HIV proteins or peptides are produced by growing host cells transformed by an exogenous or heterologous DNA construct, such as an expression vector described above under conditions whereby the HIV protein is expressed. The HIV protein or peptide is then isolated from the host cells and purified. If the expression system secretes the protein or peptide into the growth media, the protein can be purified directly from cell-free media. The selection of the appropriate growth conditions and initial crude recovery methods are within the skill of the art.

Once a coding sequence for an HIV protein or peptide of the invention has been prepared or isolated, it can be cloned into any suitable vector and thereby maintained in a composition of cells which is substantially free of cells that do not contain an HIV coding sequence. Numerous cloning vectors are known to those of skill in the art. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), plJ61 (*Streptomyces*). pUC6 (*Streptomyces*), actinophage, fC31 (Streptomyces). YIpS (*Saccharomyces*), YCp19 (*Saccharomyces*), and bovine papilloma virus (mammalian cells). See generally, Glover, supra; T. Maniatis et al., supra; and Perbal, supra.

Fusion Proteins

HIV envelope fusion proteins and methods for making such proteins have been previously described (U.S. Pat. No. 5,885,580). It is now a relatively straight forward technology to prepare cells expressing a foreign gene. Such cells act as hosts and may include, for the fusion proteins of the present invention, yeasts, fungi, insect cells, plants cells or animals cells. Expression vectors for many of these host cells have been isolated and characterized, and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extrachromosomal plasmids or after integration in whole or in part in the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector, and other factors readily appreciated by those of ordinary skill in the art.

The foreign DNA insert of interest comprises any DNA sequence coding for fusion proteins including any synthetic sequence with this coding capacity or any such cloned sequence or combination thereof. For example, fusion proteins coded and expressed by an entirely recombinant DNA sequence is encompassed by this invention but not to the exclusion of fusion proteins peptides obtained by other techniques.

Vectors useful for constructing eukaryotic expression systems for the production of fusion proteins comprise the fusion protein's DNA sequence, operatively linked thereto with appropriate transcriptional activation DNA sequences, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

Yeast expression systems, which are the preferred variety of recombinant eukaryotic expression system, generally employ *Saccharomyces cerevisiae* as the species of choice for expressing recombinant proteins. Other species of the genus *Saccharomyces* are suitable for recombinant yeast expression system, and include but are not limited to *carlsbergensis, uvarum, rouxii, montanus,kluyveri, elongisporus, norbensis, oviformis*, and *diastaticus*. *Saccharomyces cerevisiae* and similar yeasts possess well known promoters useful in the construction of expression systems active in yeast, including but not limited to GAP, GAL10, ADH2, PHO5, and alpha mating factor.

Yeast vectors useful for constructing recombinant yeast expression systems for expressing fusion proteins include, but are not limited to, shuttle vectors, cosmid plasmids, chimeric plasmids, and those having sequences derived from two micron circle plasmids. Insertion of the appropriate DNA sequence coding for fusion proteins into these vectors will, in principle, result in a useful recombinant yeast expression system for fusion proteins where the modified vector is inserted into the appropriate host cell, by transformation or other means. Recombinant mammalian expression system are another means of producing the fusion proteins for the vaccines/immunogens of this invention. In general, a host mammalian cell can be any cell that has been efficiently cloned in cell culture. However, it is apparent to those skilled in the art that mammalian expression options can be extended to include organ culture and transgenic animals. Host mammalian cells useful for the purpose of constructing a recombinant mammalian expression system include, but are not limited to, Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, *DNA Cloning. A Practical Approach*, Vols. 1-4 (Oxford, IRL Press, 1985).

Fusion proteins may possess additional and desirable structural modifications not shared with the same organically synthesized peptide, such as adenylation, carboxylation, glycosylation, hydroxylation, methylation, phosphorylation or myristylation. These added features may be chosen or preferred as the case may be, by the appropriate choice of recombinant expression system. On the other hand, fusion proteins may have its sequence extended by the principles and practice of organic synthesis.

Vaccines and Immunogenic Compositions

When used in vaccine or immunogenic compositions, the proteins or peptides of the present invention may be used as "subunit" vaccines or immunogens. Such vaccines or immunogens offer significant advantages over traditional vaccines in terms of safety and cost of production; however, subunit vaccines are often less immunogenic than whole-virus vaccines, and it is possible that adjuvants with significant immunostimulatory capabilities may be required in order to reach their full potential.

Currently, adjuvants approved for human use in the United States include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), Muramyl dipeptide (MDP) (see Ellouz et al., 1974), synthetic analogues of MDP (reviewed in Chedid et al., 1978), N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter (see EP 0399843).

The formulation of a vaccine or immunogenic compositions of the invention will employ an effective amount of the protein or peptide antigen. That is, there will be included an amount of antigen which, in combination with the adjuvant, will cause the subject to produce a specific and sufficient immunological response so as to impart protection to the subject from subsequent exposure to an HIV virus. When used as an immunogenic composition, the formulation will contain an amount of antigen which, in combination with the adjuvant, will cause the subject to produce specific antibodies which may be used for diagnostic or therapeutic purposes.

The vaccine compositions of the invention may be useful for the prevention or therapy of HIV-1 infection. While all animals that can be afflicted with HIV-1 can be treated in this manner, the invention, of course, is particularly directed to the preventive and therapeutic use of the vaccines of the invention in man. Often, more than one administration may be required to bring about the desired prophylactic or therapeutic effect; the exact protocol (dosage and frequency) can be established by standard clinical procedures.

The vaccine compositions are administered in any conventional manner which will introduce the vaccine into the animal, usually by injection. For oral administration the vaccine composition can be administered in a form similar to those used for the oral administration of other proteinaceous materials. As discussed above, the precise amounts and formulations for use in either prevention or therapy can vary depending on the circumstances of the inherent purity and activity of the antigen, any additional ingredients or carriers, the method of administration and the like.

By way of non-limiting illustration, the vaccine dosages administered will typically be, with respect to the gp120 antigen, a minimum of about 0.1 mg/dose, more typically a minimum of about 1 mg/dose, and often a minimum of about 10 mg/dose. The maximum dosages are typically not as critical. Usually, however, the dosage will be no more than 500 mg/dose, often no more than 250 mg/dose. These dosages can be suspended in any appropriate pharmaceutical vehicle or carrier in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

Peptides of the invention corresponding to domains of the envelope protein such as V3 may be constructed or formulated into compounds or compositions comprising multimers of the same domain or multimers of different domains. For instance, peptides corresponding to the V3 domain may be circularized by oxidation of the cysteine residues to form multimers containing 1, 2, 3, 4 or more individual peptide epitopes. The circularized form may be obtained by oxidizing the cysteine residues to form disulfide bonds by standard oxidation procedures such as air oxidization.

Synthesized peptides of the invention may also be circularized in order to mimic the geometry of those portions as they occur in the envelope protein. Circularization may be facilitated by disulfide bridges between existing cysteine residues. Cysteine residues may also be included in positions on the peptide which flank the portions of the peptide which are derived from the envelope protein. Alternatively, cysteine residues within the portion of a peptide derived from the envelope protein may be deleted and/or conservatively substituted to eliminate the formation of disulfide bridges involving such residues. Other means of circularizing peptides are also well known. The peptides may be circularized by means of covalent bonds, such as amide bonds, between amino acid residues of the peptide such as those at or near the amino and carboxy termini (see U.S. Pat. No. 4,683,136).

In an alternative format, vaccine or immunogenic compositions may be prepared as vaccine vectors which express the HIV protein or peptide of the invention in the host animal. Any available vaccine vector may be used, including live Venezuelan Equine Encephalitis virus (see U.S. Pat. No. 5,643,576), poliovirus (see U.S. Pat. No. 5,639,649), pox virus (see U.S. Pat. No. 5,770,211) and vaccina virus (see U.S. Pat. Nos. 4,603,112 and 5,762,938). Alternatively, naked nucleic acid encoding a protein or peptide of the invention may be administered directly to effect expression of the antigen (see U.S. Pat. No. 5,739,118).

Diagnostic Reagents

The HIV protein or peptide compositions of the present invention may be used as diagnostic reagents in immunoassays to detect anti-HIV antibodies, particularly anti-gp120 antibodies. Many HIV immunoassay formats are available. Thus, the following discussion is only illustrative, not inclusive. See generally, however, U.S. Pat. Nos. 4,743,678; 4,661,445; and 4,753,873 and EP 0161150 and EP 0216191.

Immunoassay protocols may be based, for example, upon composition, direct reaction, or sandwich-type assays. Protocols may also, for example, be heterogeneous and use solid supports, or may be homogeneous and involve immune reactions in solution. Most assays involved the use of labeled antibody or polypeptide. The labels may be, for example, fluorescent, chemiluminescent, radioactive, or dye molecules. Assays which amplify the signals from the probe are also known, examples of such assays are those which utilize biotin and avidin, and enzyme-labeled and mediated immunoassays, such as ELISA assays.

Typically, an immunoassay for anti-HIV antibody will involve selecting and preparing the test sample, such as a biological sample, and then incubating it with an HIV protein or peptide composition of the present invention under conditions that allow antigen-antibody complexes to form. Such conditions are well known in the art. In a heterogeneous format, the protein or peptide is bound to a solid support to facilitate separation of the sample from the polypeptide after incubation. Examples of solid supports that can be used are nitrocellulose, in membrane or microtiter well form, polyvinylchloride, in sheets or microtiter wells, polystyrene latex, in beads or microtiter plates, polyvinlyidine fluoride, diazotized paper, nylon membranes, activated beads, and Protein A beads. Most preferably, Dynatech, Immulon® microtiter plates or 0.25 inch polystyrene beads are used in the heterogeneous format. The solid support is typically washed after separating it from the test sample.

In homogeneous format, on the other hand, the test sample is incubated with the HIV protein or peptide in solution, under conditions that will precipitate any antigen-antibody complexes that are formed, as is known in the art. The precipitated complexes are then separated from the test sample, for example, by centrifugation. The complexes formed comprising anti-HIV antibody are then detected by any number of techniques. Depending on the format, the complexes can be detected with labeled anti-xenogenic Ig or, if a competitive format is used, by measuring the amount of bound, labeled competing antibody. These and other formats are well known in the art.

Diagnostic probes useful in such assays of the invention include antibodies to the HIV-1 envelope protein. The antibodies to may be either monoclonal or polyclonal, produced using standard techniques well known in the art (See Harlow & Lane, *Antibodies. A Laboratory Manual*, (Cold Spring Harbor, Cold Spring Harbor Laboratory Press, 1988). They can be used to detect HIV-1 envelope protein by specifically binding to the protein and subsequent detection of the antibody-protein complex by ELISA, Western blot or the like. The HIV-1 envelope protein used to elicit these antibodies can be any of the variants discussed above. Antibodies are also produced from peptide sequences of HIV-1 envelope proteins using standard techniques in the art (Harlow & Lane, supra). Fragments of the monoclonals or the polyclonal antisera which contain the immunologically significant portion can also be prepared.

The following working examples specifically point out preferred embodiments of the present invention, and are not to be construed as limiting in any way the remainder of the disclosure. Other generic configurations will be apparent to one skilled in the art. All references, including U.S. or foreign patents, referred to in this application are herein incorporated by reference in their entirety.

EXAMPLES

The following methods were used in the Examples:

Reference Serum Donor Envelope Gene Cloning

The donor of the HIV-1 Neutralizing Serum (2) (Reference 2), available in the NIH AIDS Research and Reference Reagent Program (Catalog Number: 1983) is a participant in a long term cohort study at the Clinical Center, NIH (Vujcic et al., 1995). The blood used to prepare Reference 2 had been collected in the Spring of 1989. Peripheral blood mononuclear cells that had been cryopreserved from donations obtained approximately six months and one year prior to the time of Reference 2 collections were used as sources of DNA for env gene cloning. The cells had not been stored to maintain viability. DNA was extracted using phenol/chloroform from approximately $1-3 \times 10^6$ cells from each donation (Quinnan et al., 1998). The DNA was used as template in a nested polymerase chain reaction, similar to that described previously, except rTth was used as the DNA polymerase, following the manufacturer's instructions (Barnes, 1992; Cariello et al., 1991). The DNA was cloned into the expression vector pSV7d, as previously described (Quinnan et al., 1998; Stuve et al., 1987).

Other env Gene Clones and Virus Pools

The following HIV-1 env clones in the expression vector pSV3 were obtained from the AIDS Research and Reference Reagent Program, 93MW965.26 (clade C), 92RWO20.5 (clade A), 93TH966.8 (clade E), 92UG975.10 (clade G) (Gao et al., 1994). The production of env clones from the molecular virus clones NL43, AD8, and SF162 has been previously described (Quinnan et al., 1998; Adachi et al., 1986; Theodore et al., 1996; Englund et al., 1995). env gene of the Z2Z6 strain was cloned similarly, using molecular virus clone plasmid as template in polymerase chain reaction, and cloning the genes into the plasmid pSV7d (Seth et al., 1993). The production of primary isolate env clones from participants in the Multicenter AIDS Cohort Study, designated here P9 and P10, has also been previously described (Quinnan et al., 1998). P9 and P10-virus pools were prepared by single subpassages of the cell culture media from primary cultures in PHA blasts (Quinnan et al., 1998). The use of molecular virus clones for preparation of virus pools of NL43 in H9 cells, and NL(SF162) and AD8, in PHA blasts, has also been previously described (Quinnan et al., 1998).

Cell Cultures

The H9 cell line was obtained from Robert Gallo (Mann et al., 1989). The Molt 3 cell line was obtained from the American Type Culture Collection, Rockville, Md. (ATCC). (Daniel et al., 1988) The HOS cell lines expressing CD4 and various coreceptors for HIV-1 were obtained from the NIH AIDS Research and Reference Reagent Program, as was the PM1 cell line (Deng et al., 1996; Landau et al., 1992; Lusso et al., 1995). The 293T cell line was obtained from the ATCC, with permission from the Rockefeller Institute (Liou et al., 1994). The H9, Molt3 and PM1 cell cultures were maintained in RPMI-1640 medium supplemented with 10% fetal bovine serum and antibiotics (Gibco). The HOS and 293T cells were maintained in Dulbecco's Minimal Essential Medium (Gibco), with similar supplements, except that the HOS cell medium was supplemented with puromycin for maintenance of plasmid stability. Cryopreserved human peripheral blood lymphocytes were stimulated with PHA and used for virus infections (Quinnan et al., 1998; Mascola et al., 1994).

Reverse Transcriptase Assay

Reverse transcriptase activity was assayed as previously described (Park et al., 1998).

Virus Neutralization Assays

The virus NL43 was used in neutralization assays which employed Molt3 cells as target cells and used giant cell formation for endpoint determination, as previously described (Vujcic et al., 1995). The amounts of virus used were sufficient to result in the formation of 30-50 giant cells per well (Vujcic et al., 1995; Lennette, 1964). The viruses, NL(SF162) and AD8, P9 and P10 were tested for neutralization in PHA stimulated human lymphoblasts in the presence of IL-2 (Quinnan et al., 1998; Mascola et al., 1994). In the latter assays ten percent of the cell suspension was removed each week, fifty percent of the medium was changed each week, and medium was sampled twice weekly from each well for reverse transcriptase assay. The reverse transcriptase assays were performed on the test samples from the first sampling date at which the non-neutralized control wells had reverse transcriptase activity about 10-20×background, generally on day 14 or 17 of the assay. The neutralization endpoint was considered to be the highest dilution of serum at which reverse transcriptase activity was reduced at least fifty percent. The Reference Neutralizing Sera 1 and 2 and the Negative Reference Serum were used as positive and negative controls (NIH AIDS Research and Reference Reagent Program)

Pseudovirus Construction and Assays of Pseudoviruses for Infectivity and Neutralization Pseudoviruses were constructed and assayed using methods similar to those described previously (Quinnan et al., 1998; Deng et al., 1996; Park et al., 1998). pSV7d-env plasmid DNA and pNL43.luc+.E-R- were cotransfected into 70 to 80% confluent 293T cell cultures using the calcium phosphate/Hepes buffer technique, following manufacturer's instructions (Promega, Madison, Wis.), in 24 well plastic tissue culture trays or 25 $cm^2$ flasks (Quinnan et al., 1998; Deng et al., 1996; Park et al., 1998). After 24 hours the medium was replaced with medium containing one mM sodium butyrate (Quinnan et al., 1998; Park et al., 1998). Two days after transfection medium was harvested, passed through a 45 μm sterile filter (Millipore Corp, Bedford, Mass.), supplemented with an additional 20% fetal bovine serum and stored at −80° C.

Pseudovirus infectivity was assayed in PM1 or HOS-CD4 cells expressing various co-receptors. Transfection supernatants were serially diluted and inoculated into cells in 96 well plates, 50 μl per well. Assays were routinely performed in triplicate. The cultures were incubated for four days, centrifuged at 400×g for ten minutes if PM1 cells were used, and medium removed by aspiration. The cells were washed twice with phosphate buffered saline, lysed with 25 μl cell culture lysing reagent according to the manufacturer's instructions (Promega, Madison, Wis.); the cells were then tritated into the medium, and 10 μl of the suspensions were transferred to wells of 96 well luminometer plates. Substrate was added in 100 μl volumes automatically, and the luminescence read using a MicroLumatPlus luminometer (EG&G Berthold, Hercules, Calif.). Mock PV controls were used in each assay consisting of media harvested from 293T cell cultures transfected with pSV7d (without an env insert) and pNL43.Luc.E-R-, and processed in the same way as cultures for PV preparation. Infectivity endpoints were determined by a modified Reed Munch method; an individual well was considered positive if the luminescence was at least 10-fold greater than the mock control, and the endpoint was considered to be the highest dilution at which the calculated frequency of positivity was ≧50% (Quinnan et al., 1998; Park et al., 1998; Lennette, 1964). Luminescence resulting from infection with minimally diluted samples was generally about 10,000-fold greater than background.

Neutralization tests were performed using PM1 or HOS-CD4 cells. Aliquots of 25 μl of two-fold serial serum dilutions were mixed with equal volumes of diluted PV in wells of 96 well plates. The PV dilutions were selected so as to expect luminescence in the presence of non-neutralizing serum of about 100-fold of background. Assays were performed in triplicate. The virus serum mixtures were incubated for sixty minutes at 40° C., after which 150 μl aliquots of PM1 cell suspensions were added, which each contained $1.5×10^4$ cells, or the suspensions were transferred to wells containing HOS-CD4 cells. The assays were then processed similarly to the infectivity assays. The neutralization endpoints were calculated by a modified Reed-Munch method in which the endpoint was considered to be the highest serum dilution calculated to have a frequency of ≧50% for reducing luminescence by ≧90% compared to the non-neutralized control. PV titrations were conducted in duplicate in parallel with each neutralization assay.

Nucleic Acid Sequencing

Nucleotide sequence analysis was performed using the di-deoxy cycle sequencing technique and AmpliTaq FS DNA polymerase, according to manufacturer's directions (Perkin Elmer Applied Biosystems, Foster City, Calif.). After the sequencing reaction the DNA was purified using Centriflex Gel Filtration Cartridges (Advanced Genetic Technologies, Gaithersburg, Md.). Sequencing gels were run and analyzed using an Applied Biosystems Prism, Model 377 DNA Sequencer. Sequencing was performed on both strands. Sequence alignment was performed using the Editseq SEQ-MAN, and Megalign programs in DNA Star according to the method of Higgins and Sharp (1989).

Example 1

Comparability of Clones Isolated from Different Time Points

From the samples of patient cells from each of the two time points, env clones were recovered which encoded proteins which were capable of mediating pseudovirus entry into target cells. Two such clones from each time point were further characterized. As shown in Table 1, the envelopes of all four clones mediated infection for PM1 cells and were neutralized comparably by References 1 and 2. Pseudoviruses carrying envelopes corresponding to each clone were also tested for infectivity for HOS-CD4 cells expressing either CXCR4 or CCR5, and all four were infectious only for the cells expressing CCR5, as shown in Table 2. Nucleotide sequences including the V3 regions were analyzed for each clone, with more than 300 bases assigned for each, and no differences between the clones were found (results not shown). Based on the absence of demonstration of differences in these assays, a single clone from the March sample was selected for use in subsequent assays, and is designated R2, hereafter.

Example 2

Clone R2 Genotype and Host Range Phenotype

The complete nucleotide sequence of the env gene clone R2 was determined and found to have an open reading frame of 2598 bases (Genbank Accession Number: AF 128126) (SEQ ID NO: 24). The amino acid sequence deduced from this sequence is shown in Table 3 (SEQ ID NO: 1). There are thirty predicted glycosylation sites, compared to twenty-nine in the consensus clade B sequence; four consensus glycosylation sites are lacking in R2, including those at residues 146, 215, 270 and 368 (numbering according to the Human Retroviruses and AIDS Database clade B consensus sequence), in the V2, C2, C2 and V4 regions of gp120, respectively (Myers et al., 1993). The consensus glycosylation sequences at residues 215 and 270 are highly and moderately variable, respectively.

Genotypic analyses conducted included evaluation of the gp120 and gp41 nucleotide coding sequences in comparison to those of a number of strains of clades A through G, as shown in FIG. 1 (Saitou et al., 1987; Myers & Miller, 1988). Both coding regions were more closely related to clade B than non-clade B sequences. Comparative analyses of regions of the predicted gp120 and gp41 amino acid sequences were also performed (results not shown). The regions analyzed included: each constant and variable region of gp120; the proximal gp41 ectodomain including the leucine zipper region; the part of gp41 extending from the end of the leucine zipper to the second cysteine; the remaining gp41 ectodomain, and the transmembrane region; and the cytoplasmic region. R2 consistently related more closely with the clade B sequences than the others.

Example 3

Figure 2:
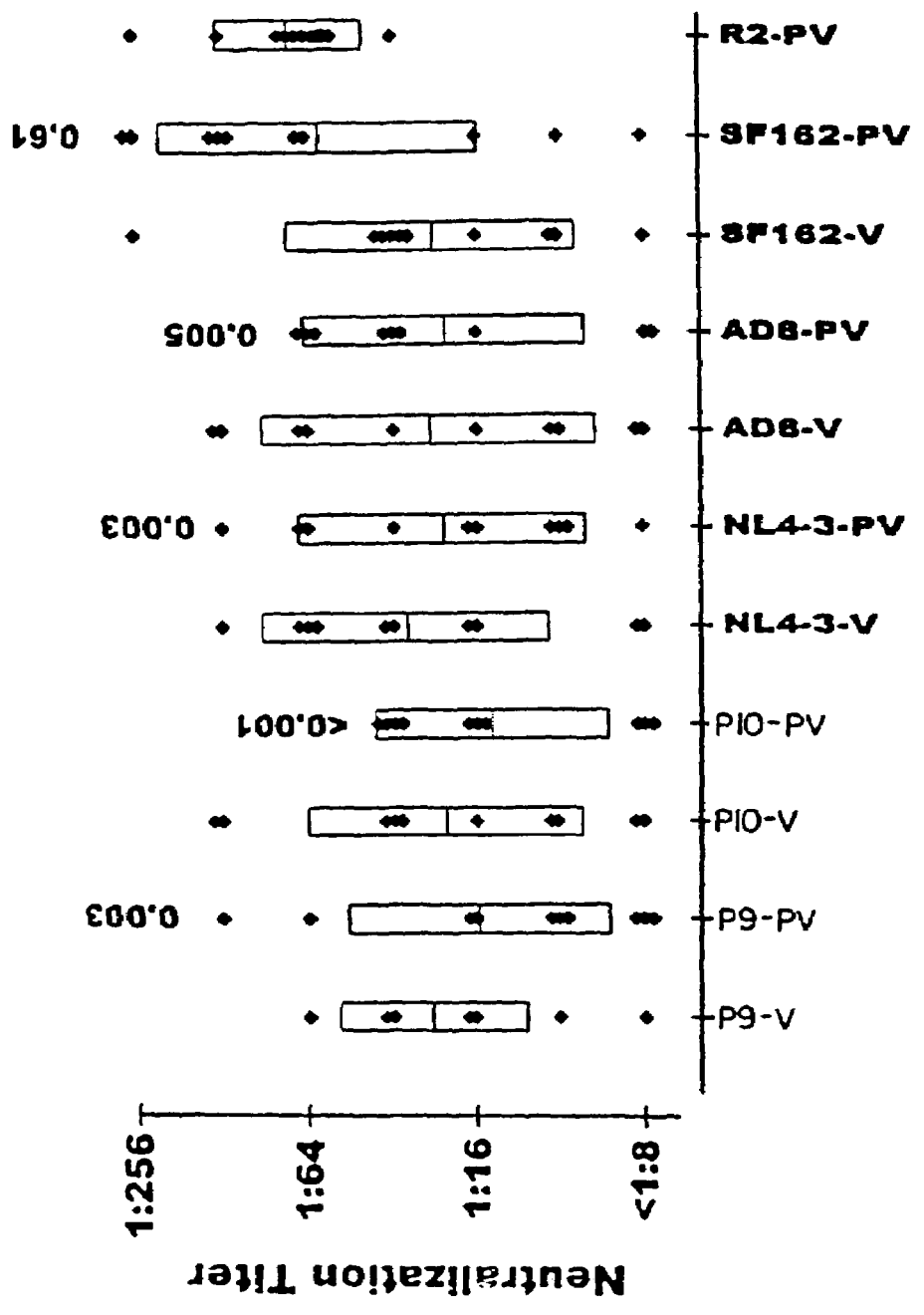

Comparative Sensitivity of R2 and Other Clade B Viruses and Pseudoviruses to Neutralization by Sera from Individuals with Clade B Infections The neutralization of R2 pseudovirus was compared to other clade B viruses and pseudoviruses as shown in FIG. 2. Of the five virus-pseudovirus comparisons made (P9, PI O, NL43, AD8 and SF162 V and PV), there were no significant differences in the neutralization of matched viruses and pseudoviruses by paired t test (statistical results not shown). Each of the pseudovirus preparations was neutralized by seven, eight, or nine of the sera tested, and the geometric mean titers ranged from 1:13.9 to 1:56, while the R2-PV was neutralized by all ten of the sera tested, with a geometric mean titer of 1:73.5. Although the neutralization titers of each of the different sera against R2 and the other pseudoviruses were frequently within four-fold, the neutralization of R2-PV was significantly greater by paired t test than four of the other PV preparations.

Example 4

Comparative Neutralization of Pseudoviruses Expressing R2 and Other Envelopes of Diverse Subtypes by Sera from Diverse Subtype Infections The results of comparative neutralization testing using sera from individuals infected with HIV-1 strains of subtypes A, C and E, and the Reference 1 and 2, and one Thai clade B serum are shown in Table 4. Reference 2 neutralized the pseudovirus expressing the homologous R2 envelope at the modest titer of 1:64 in the experiment shown and within two-fold of this titer in many other experiments. It neutralized the other seven pseudoviruses tested at low to moderate titers, as well. The R2 pseudovirus was neutralized by seventeen of twenty-four sera, including sera from people infected with each of the clades A-F. The other two clade B pseudoviruses were neutralized less frequently and were also neutralized infrequently by the clade E sera. The frequency of neutralization by sera from individuals infected with different clades was not significantly skewed for any of the other four pseudoviruses. Clade A, C, D and G pseudoviruses were neutralized by eight, seventeen, six and three of the seventeen sera tested, respectively. The clade C pseudovirus was substantially more sensitive to neutralization, in general than the others tested. The dade E pseudovirus was neutralized by five of five clade D sera and seven of eight clade E sera but only one of the sera from people infected by other clades.

Example 5

Synthetic Peptides Generated from V3 Amino Acid Sequences from R2 Strain

R2 strain V3 peptides were synthesized using an automated ABI synthesizer and FMOC chemistry (Zeng et al., 1997). The sequences of these peptides were KSIPMGPGRAFYT-TGQI (SEQ ID NO:2) and CSRPNNNTRKSIPMG-PGRAFYTTGQIIGDIRQAHC (SEQ ID NO:3). The mutant R2(313-4PM/HI, 325Q/D) V3 peptide was prepared similarly. Strain 93TH966.8 V3 peptide, sequence: CTRPSNNTRTSTTIGPGQVFYRTGDITGNIRKAYC (SEQ ID NO:4) was synthesized using the same methods. The peptides were purified using C 18, acetonitrile-in-water gradient chromatography with a Waters High Performance Liquid Chromatograph. Sequences of the purified peptides were verified using an ABI automated sequencer. Peptides were lyophilized and stored at 4-8° C. Preparation of a linear MN strain V3 peptide has been described previously (Carrow et al., 1991). Cyclic MN strain 35-mer peptide was obtained from the AIDS Research and Reference Reagent Program (Catalog #1841) provided by Catasti et al., (1996).

The R2 V3 35-mer was insoluble in water, while all other peptides tested were soluble in water to at least 10 mg/ml. To obtain cyclic peptides, solutions of the R2 and R2(313-4PM/HI, 325Q/D) V3 35-mers in dimethylsulfoxide (DMSO), 10 mg/ml, were diluted 1:10 in water at room temperature or 37° C. and the pH was adjusted to 8.5 with ammonium hydroxide. These solutions were aerated by bubbling air through the solutions for periods ≧1 hour. Following aeration, the pH was adjusted to 7.4 using hydrochloric acid. A portion of the R2 35-mer peptide precipitated during these procedures. To obtain an approximate quantitation of the amount of R2 V3 35-mer that remained in solution, the turbidity of the suspension was determined at 480 nm wavelength visible light using a spectrophotometer. The spectrophotometer was blanked with a solution of 10 percent DMSO in water, and a standard curve was produced using slurries of known amounts of the 35-mer peptide suspended in water. The amount of precipitate estimated by turbidity was subtracted from the amount of peptide added at the beginning of the preparation procedure to estimate the amount remaining in solution. The solubility of the oxidized R2 35-mer peptide in 10 percent DMSO solution at pH=7.4 was estimated to be 300-350 μg/ml when processed at room temperature, or 850-900 μg/ml when processed at 37° C. Peptides were sterilized by passage through 0.22μ pore size filters prior to use.

Example 6

Figure 3A:
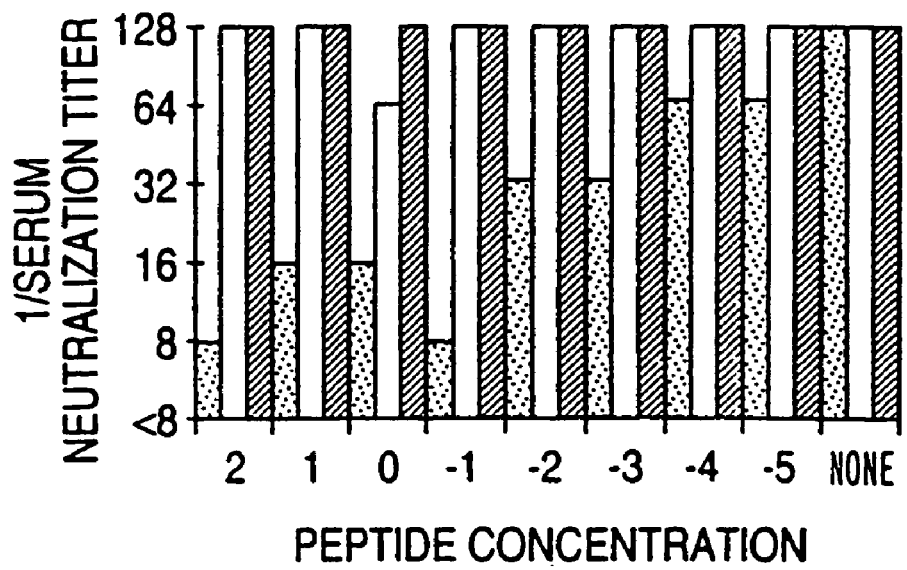
FIG. 3 (A): Inhibition of Reference 2-mediated neutralization of pseudoviruses by synthetic V3 peptides. The neutralization endpoints for 90% neutralization were calculated as described previously (Quinnan et al., 1999; Quinnan et al., 1998; Zhang et al., 1999; Park et al., 1998). Results shown are means of triplicate determinations. Dose-response effects of R2 linear 17-mer (open square) and cyclic (closed square) (SEQ ID NO:2) and the 93TH966.8 cyclic (shaded square) (SEQ ID NO:3) V3 peptides on neutralization of clone R2 pseudovirus. The peptide concentrations are 3×10 raised to the indicated power.

Peptide Blocking of Neutralizing Antibody Activity Against Clone R2 Pseudovirus The neutralization blocking effects of synthetic V3 peptides were examined to test the contribution of V3-anti-V3 interactions in the neutralizing cross reactivities of Reference 2 and clone R2. The blocking effects of peptides on neutralizing activity of Reference 2 against clone R2 pseudovirus are shown in FIG. 3A. Usually, the linear 17-mer peptide had no inhibitory effect on neutralization, as shown. In only one of several experiments two-fold reduction of neutralization was observed in the presence of 17-mer peptide. Concentration-dependent inhibitory effects of the cyclic 35-mer R2 V3 peptide on neutralization of clone R2 pseudovirus by Reference 2 was observed in the experiment shown and in numerous other similar experiments. Maximum effect was observed at approximately 15 μg/ml. No inhibitory effect was observed using a cyclic peptide homologous to the V3 region of the HIV-1 93TH966.8 strain.

Figure 3B:
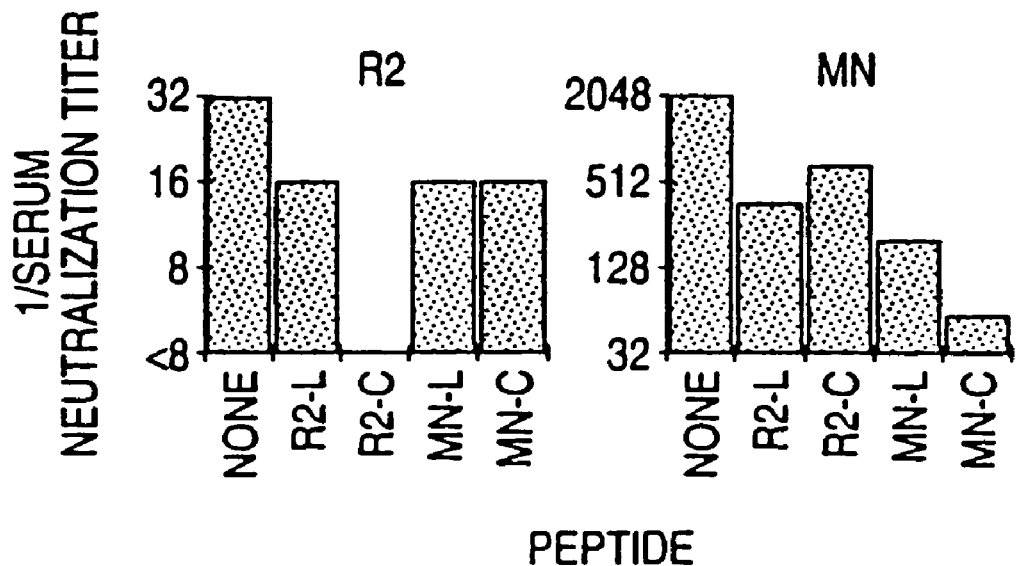

The comparative effects of the R2 and MN strain V3 peptides on neutralization of the R2 and MN strain pseudoviruses are shown in FIG. 3B. The results shown are representative of two additional experiments. Only the cyclic R2 V3 peptide produced consistent blocking of R2 pseudovirus neutralization. The linear R2 and MN, and the cyclic MN peptides did not block R2 neutralization in two experiments and blocked only two-fold in a third experiment. In contrast, the MN cyclic and linear peptides consistently inhibited MN strain neutralization eight- to sixteen-fold in these experiments, and the R2 peptides had consistent two-fold inhibitory effects on neutralization of the MN strain. These effects of MN peptides on MN strain neutralization are consistent with previous reports (Carrow et al., 1991; Park et al., 1999).

Example 7

Cyclic R2 V3 Peptide Inhibition of Neutralization of R2 Pseudoviruses by Sera from MACS Patients Inhibition of heterologous serum neutralization of R2 pseudovirus by cyclic R2 V3 peptide was evaluated to determine if cross reactivity of these sera with R2 included effects of anti-V3 antibodies. The comparative neutralization titers of sera from ten patients from the MACS against clone R2 pseudovirus in the presence and absence of cyclic R2 V3 peptide are shown in FIG. 4A (Quinnan et al., 1998). These sera have been described previously, and have been shown to neutralize primary HIV-1 enveloped pseudoviruses cross reactively, but to a lesser extent than Reference 2 (Zhang et al., 1999). Each serum was tested twice. Seven of the sera appeared to be inhibited at least two-fold in one or both experiments. The geometric mean inhibitory effect of all the tests was 1.9-fold. The results of twelve tests conducted at the same times as those tests shown in FIGS. 4A and 4B are shown for Reference 2; the geometric mean inhibitory effect was 3.56.

Example 8

Cyclic R2 V3 Peptide Inhibition of Reference 2 Neutralization of Pseudoviruses Expressing Envelopes from the MACS Patients Inhibition of Reference 2 neutralization of pseudoviruses expressing heterologous envelopes by cyclic R2 V3 peptide was evaluated to determine whether anti-V3 antibody contributed to the neutralizing cross reactivity of Reference 2. The results of these experiments are shown in FIG. 4B. Each pseudovirus was tested two or three times. The peptide appeared to exert a two-fold inhibitory effect in one, two, or three of the experiments using each of the six pseudoviruses. The geometric mean inhibitory effect was 1.6-fold.

Example 9

Induction of Cross-Reactive Neutralizing Antibodies in Mice Following Immunization with Recombinant Delivery Vectors Encoding Hiv-1 Envelope Proteins The DNA clone encoding the R2 envelope was introduced into an expression vector which can be used to express the envelope protein complex in vivo for immunization. The recombinant delivery vector expressing the R2 envelope clone was been administered to mice, both in its full length, encoding both gp120 and gp41, or in a truncated form. The truncated form is secreted by cells which express gp140. Both the full-length and truncated form of these constructs induced neutralizing antibodies in mice. The mice which received the gp140 construct, which includes the V3 region, have developed neutralizing antibodies which neutralize at least three different strains of HIV-1, including the R2 strain, a macrophage tropic laboratory strain known as SF162, and a primary strain which is not laboratory adapted. The amount of cross-reactivity observed exceeds that induced by most or all other HIV immunogens that have been tested as single agents.

TABLE 1

Comparative Neutralization of Pseudoviruses Expressing Multiple Envelope Clones From Donor 2

| Serum | Neutralization Titer Against Clone | | | |
|---|---|---|---|---|
| | 10.1 | 10.2 | 3.1 | 3.2 |
| Reference 1 | 1:32 | 1:64 | 1:32 | 1:64 |
| Reference 2 | 1:128 | 1:128 | 1:128 | 1:128 |

TABLE 2

Coreceptor Dependency of R2 Pseudovirus Entry Into HOS-CD4 Cells

| Pseudovirus | Infectivity Titer | | | | | | |
|---|---|---|---|---|---|---|---|
| | In HOS-CD4 Cells Expressing | | | | | | |
| | CCR1 | CCR2b | CCR3 | CCR4 | CCR5 | CXCR4 | In PM1 Cells |
| R2 | <1:4 | <1:4 | <1:4 | <1:4 | 1:64 | <1:4 | 1:32 |
| P9 | <1:4 | <1:4 | <1:4 | <1:4 | 1:256 | <1:4 | 1:8 |
| NL4-3 | <1:4 | <1:4 | <1:4 | <1:4 | 1:32 | >1:256 | 1:8 |
| AD8 | <1:4 | <1:4 | <1:4 | <1:4 | 1:256 | <1:4 | 1:32 |

TABLE 3

Inferred Amino Acid Sequence of the R2 Envelope Clone from Donor 2.

| Amino Acid Residue[a] | | | | Residue Number |
|---|---|---|---|---|
| MRVKGIRRNY | QHWWGWGTML | LGLLMICSAT | EKLWVTVYYG VPVWKEATTT | 50 |
| LFCASDAKAY | DTEAHNVWAT | HACVPTDPNP | QEVELVNVTE NFNMWKNNMV | 100 |
| EQMHEDIISL | WDQSLKPCVK | LTPLCVTLNC | TDLRNTTNTN NSTDNNNSNS | 150 |
| EGTIKGGEMK | NCSFNAITSI | GDKNQKEYAL | LYKLDIEPID NDNTSYRLIS | 200 |

TABLE 3-continued

Inferred Amino Acid Sequence of the R2
Envelope Clone from Donor 2.

| Amino Acid Residue[a] | Residue Number |
|---|---|
| CNTSVITQAC PKISFEPIPI HYCAPAGEAT LKCNDKKFSG KGSCKNVSTV | 250 |
| QCTHGIRPVV STQLLLNGSL AEEEVVIRSE NFTNNAKTII VQLREPVKIN | 300 |
| CSRPNNNTRK SIPMGPGRAF YTTGQIIGDI RQAHCNISKT NWTNALKQVV | 350 |
| EKLGEQFNKT KIVFTNSSGG DPEIVTHSFN CAGEFFYCNT TQLFDSIWNS | 400 |
| ENGTWNITRG LNNTGRNDTI TLPCRIKQII NRWQEVGKAM YAPPIKGNIS | 450 |
| CSSNITGLLL TRDGGKDDNS RDGNETFRPG GGDMRDNWRS ELYKYKVVKI | 500 |
| EPLGVAPTKA KRRVVQREER AVGLGAMFIG FLGAAGSTMG AASVTLTVQA | 550 |
| RQLLSGIVQQ QSNLLRAIEA QQHLLQLTVW GIKQLQARIL AVERYLKDQQ | 600 |
| LLGIWGCSGK LICTTTVPWN ASWSKNKTLE AIWNNMTWMQ WDKEIDNYTS | 650 |
| LIYSLIEESQ IQQEKNEQEL LELDKWANKW NWFDISNWLW YIKIFIMIVG | 700 |
| GLVGLRIVFV VLSIVNRVRQ GYSPLSFQTR LPAPRGPDRP EEIEEEGGDR | 750 |
| DRDRSGLLVD GFLTLIWVDL RSLCLFSYHR LRDLLLIVTR IVELLGRRGW | 800 |
| EILKYWWNLL QYWSQELKNS AVSLFNATAI AVAEGTDRVI EVLQRVGRAL | 850 |
| LHIPTRIRQG LERALL | 866 |

[a]Amino Acid residues are identified by standard single letter designations. Predicted N-linked glycosylation sites are indicated by shading and bolding.

TABLE 4

Neutralization of Pseudoviruses Expressing Envelopes of Various Clades by Sera from People Infected with Various Clades of HIV-1

| | | NA Titer Against Pseudovirus (Clade)[a] | | | | | | | |
|---|---|---|---|---|---|---|---|---|---|
| Clade | Serum[b] | R2 (B) | P9 (B) | P10 (B) | RW020 (A) | MW965 (C) | Z2Z6 (D) | TH966 (E) | UG975 (G) |
| B | Ref 1 | 32 | 16 | 32 | <10 | 256 | 10 | <8 | <10 |
| | Ref 2 | 64 | 32 | 64 | 10 | 128 | 40 | 8 | 10 |
| | WR8465 | 20 | NT[c] | 80 | <10 | 640 | 10 | <10 | 10 |
| A | 37570 | 320 | 160 | 20 | 80 | 2560 | <10 | <10 | <10 |
| | 35374 | 40 | <10 | <10 | <10 | 640 | <10 | <10 | <10 |
| | 35837 | 40 | 20 | <10 | 80 | 2560 | <10 | <10 | <10 |
| C | 5107 | 40 | 10 | <10 | 10 | 1280 | <10 | <10 | <10 |
| | 5708 | 10 | <10 | <10 | <10 | 320 | <10 | <10 | <10 |
| | 5218 | 80 | <10 | <10 | <10 | 1280 | <10 | <10 | <10 |
| D | UG9240 | <10 | NT | NT | NT | NT | NT | 20 | NT |
| | UG9370 | <10 | NT | NT | NT | NT | NT | 10 | NT |
| | UG9386 | <10 | NT | NT | NT | NT | NT | 10 | NT |
| | UG93097 | 10 | NT | NT | NT | NT | NT | 10 | NT |
| | UG94118 | 10 | NT | NT | NT | NT | NT | 20 | NT |
| E | WR5659 | 10 | <10 | <10 | <10 | 20 | <10 | 40 | <10 |
| | WR5901 | <10 | <10 | <10 | 40 | 320 | 10 | 40 | 10 |
| | WR8177 | <10 | <10 | <10 | 40 | 640 | 10 | 80 | <10 |
| | WR8657 | <10 | <10 | 10 | 10 | 640 | <10 | 80 | <10 |
| | WR8593 | <10 | <10 | <10 | <10 | 160 | 10 | 40 | <10 |
| | 1008 | <10 | <10 | <10 | <10 | 10 | <10 | <10 | <10 |
| | 1053 | 20 | <10 | <10 | <10 | 40 | <10 | 20 | <10 |
| | 1062 | 20 | 10 | <10 | 10 | 320 | <10 | 20 | <10 |
| F | BR9318 | <10 | NT | NT | NT | NT | NT | <10 | NT |
| | BR93019 | 10 | NT | NT | NT | NT | NT | <10 | NT |

TABLE 4-continued

Neutralization of Pseudoviruses Expressing Envelopes of Various Clades by Sera from People Infected with Various Clades of HIV-1

| Clade Serum[b] | NA Titer Against Pseudovirus (Clade)[a] | | | | | | | |
|---|---|---|---|---|---|---|---|---|
| | R2 (B) | P9 (B) | P10 (B) | RW020 (A) | MW965 (C) | Z2Z6 (D) | TH966 (E) | UG975 (G) |
| BR93020 | 20 | NT | NT | NT | NT | NT | <10 | NT |
| BR93029 | 10 | NT | NT | NT | NT | NT | <10 | NT |

[a]Neutralization titers are the dilutions at which 90% inhibition of luminescence was observed.
[b]Sera were the Reference Neutralizing Human Serum 1 and 2, or were provided by Dr. J. Mascola, HIVNET, or the UNAIDS Program, as described in the text.
[c]NT = not tested.

TABLE 5

Comparison of V3 Region Amino Acid Sequences of Clone R2 with Phenetic Subgroup Consensus Sequences 1 Through 13 and Clade A Through E Consensus Sequences.[a]

| Clone, Subgroup or Clade | V3 Region Amino Acid Sequence |
|---|---|
| R2 | NNTR.KSIPMGPGRAFYTTGQIIGDIRQAHC |
| PHENETIC 1 (SEQ ID NO: 6) | ----.---HI----------D---------- |
| PHENETIC 2 (SEQ ID NO: 7) | ----.---SI-------A--E---------- |
| PHENETIC 3 (SEQ ID NO: 8) | ----.---SI-------A--K---------- |
| PHENETIC 4 (SEQ ID NO: 9) | ----.---RI---Q---A--D---------- |
| PHENETIC 5 (SEQ ID NO: 10) | ----.---HI-------A--K---------- |
| PHENETIC 6 (SEQ ID NO: 11) | K--RRR-H.I---------K---------- |
| PHENETIC 7 (SEQ ID NO: 12) | ----.T--TI---QV--R--K---------- |
| PHENETIC 8 (SEQ ID NO: 13) | KKM-.T-ARI----V-HK--K---S-TK-Y- |
| PHENETIC 9 (SEQ ID NO: 14) | ----.Q-THI---A-L---.D---K------ |
| PHENETIC 10 (SEQ ID NO: 15) | ----.QGTHI-----Y---.N---------- |
| PHENETIC 11 (SEQ ID NO: 16) | ----.QRSTI-Q-QAL---.E-R------A- |
| PHENETIC 12 (SEQ ID NO: 17) | D-IKIQRT-I-Q-Q-L---RITGYI.G---- |
| PHENETIC 13 (SEQ ID NO: 18) | Q-K-.QGT-I-L-Q-L---R.-K----K--- |
| CLADE A (SEQ ID NO: 19) | ----.--VHI---Q---A--D---------- |
| CLADE B (SEQ ID NO: 20) | ----.---HI----------E---------- |
| CLADE C (SEQ ID NO: 21) | ----.---RI---QT-YA--D---------- |
| CLADE D (SEQ ID NO: 22) | ----.QRTHI---Q-L---.R---------- |
| CLADE E (SEQ ID NO: 23) | ----.T--TI---QV--R--D------K-Y- |

[a]Dashes indicate residues at which the individual sequences are identical to R2. The periods indicate sites of insertions or deletions.

REFERENCES

Adachi A, Gendelman H E, Keonig S, Folks T, Wiley R, Rabson A and Martin M A, *Production of acquired immunodeficiency syndrome-associated retrovirus in human and nonhuman cells transfected with an infectious molecular clone*. J. Virol. (1986) 59: 284-291.

Back N K, Smit L, Schutten M, Nara P L, Tersmette M and Goudsmit J, *Mutations in human immunodeficiency virus type 1 gp41 affect sensitivity to neutralization by gp120 antibodies*. J. Virol. (1993) 67: 6897-6902.

Barnes W M, *The fidelity of Taq polymerase catalyzing PCR is improved by an N-terminal deletion*. Gene (1992) 112: 29-35.

Baumann H, Gelehrter T D and Doyle D, *Dexamethasone regulates the program of secretory glycoprotein synthesis in hepatoma tissue culture cells*. J. Cell Biol. (1980) 85: 1-8.

Cariello N F, Swenberg J A and Skopek T R, *Fidelity of Thermococcus litoralis DNA polymerase (Vent) in PCR determined by denaturing gradient gel electrophoresis*. Nucleic Acids Res. (1991) 19: 4193-4198.

Catasti P, Bradbury E M and Gupta G. *Structure and polymorphism of HIV-1 third variable loops*. J Biol. Chem. (1996) 271: 8236-8242.

Carrow E W, Vujcic L K, Glass W L, Seamon K B, Rastogi S C, Hendry R M, Boulos R, Nzila N and Quinnan G V. *High prevalence of antibodies to the gp120 V3 region principal neutralizing determinant of HIV-1 MN in sera from Africa and the Americas*. AIDS Res Hum Retroviruses (1991) 7: 831-838.

Chackerian B, Rudensey L M and Overbaugh J. *Specific N-linked and O-linked glycosylation modifications in the envelope V1 domain of simian immunodeficiency virus variants that evolve in the host alter recognition by neutralizing antibodies*, J Virol (1997) 71: 7719-7727.

Chedid L, Audibert F and Johnson A G, *Biological activities of muramyl dipeptide, a synthetic glycopeptide analogous to bacterial immunoregulating agents*. Prog Allergy (1978) 25: 63-105.

Daniel M D, Li Y, Naidu Y M, Durda P J, Schmidt D K, Troup C D, Silva D P, MacKey J J, Kestler H W, Sehgal P K et al., *Simian immunodeficiency virus from African green monkeys*. J. Virol. (1988) 62: 4123-4128.

Deng H, Liu R, Ellmeier W, Choe S, Unutmaz D, Burkhart M, Di Marzio P, Marmon S, Suttom R E, Hill C M, Davis C B, Peiper S C, Schall T J, Littman D R and Landau N L, *Identification of a major co-receptor for primary isolates of HIV*. Nature (1996) 381: 661-666.

D'Souza M P, Durda P, Hanson C V, Milman G and collaborating investigators, *Evaluation of monoclonal antibodies to HIV-1 by neutralization and serological assays: an international collaboration*. AIDS (1991) δ: 1061-1070.

Ellouz F, Adam A, Ciorbaru R and Lederer E, *Minimal structural requirements for adjuvant activity of bacterial peptidoglycan derivatives*. Biochem Biophys Res Commun. (1974) 59: 1317-1325.

Englund G, Theodore T S, Freed E O, Engleman A and Martin M A, *Integration is required for productive infection of monocyte-derived macrophages by human immunodeficiency virus type 1*. J. Virol. (1995) 69: 3216-3219.

Fortin J F, Cantin R and Tremblay M J, *T cells expressing activated LFA-1 are more susceptible to infection with human immunodeficiency virus type 1 particles bearing host-encoded ICAM*. J. Virol. (1998) 72: 2105-2112.

Gao F, Yue L, Craig S, Thornton C L, Robertson D L, McCutchan F E, Bradac J A, Sharp P M and Hahn B H, *Genetic variation of HIV type 1 in four World Health Organization-sponsored vaccine evaluation sites: generation of functional envelope (glycoprotein 160) clones representative of sequence subtypes A, B, C and E. WHO Network for HIV Isolation and Characterization*. AIDS Res Hum Retroviruses (1994) 10: 1359-1368.

Ghiara J B, Stura E A, Stanfield R L, Profy A T and Wilson I A, *Crystal structure of the principal neutralization site of HIV*. Science (1994) 264: 82-85.

Higgins D G and Sharp P M, *Fast and sensitive multiple sequence alignments on a microcomputer*. CABIOS (1989) 5: 151-153.

Hioe C E, Xu S, Chigurupati P, Burda S, Williams C, Gorny M K and Zolla-Pazner S, *Neutralization of HIV-1 primary isolates by polyclonal and monoclonal human antibodies*. Int Immunol. (1997) 9: 1281-1290.

Korbert B T, MacInnes K, Smith R F and Myers G, *Mutational trends in V3 loop protein sequences observed in different genetic lineages of human immunodefciency virus type 1*. J. Virol. (1994) 68: 6730-6744.

Landau N R and Littman D R, *Packaging system for rapid production of murine leukemia virus vectors with variable tropism*. J. Virol. (1992) 66: 5110-5113.

Lennette E H. "General principles underlying laboratory diagnosis of viral and rickettsial infections" in: Lennette E H and Schmidt M J, *Diagnostic Procedures of Viral and Rickettsial Disease* (New York, American Public Health Association, 1964) pp. 45

Liou H C, Sha W C, Scott M L and Baltimore D, *Sequential induction of NF-kappa B/Rel family proteins during B-cell terminal differentiation. Mol Cell Biol.* (1994) 14: 5349-5359.

Luciw P A. in: Fields B N, Knipe D M and Howley P M, Fields Virology, 3d ed, (Philadelphia, Lippincott-Raven, 1996), pp 1881-952.

Lusso P, Cocchi F, Balotta C, Markham P D, Louie A, Farci P, Pal R, Gallo R C and Reitz M S, *Growth of macrophage-tropic and primary human immunodeficiency virus type 1 (HIV-1) isolates in a unique CD4+ T-cell clone (PM1): failure to downregulate CD4 and to interfere with cell-line HIV-1*. J. Virol. (1995) 69: 3712-3720.

Mackett M, Smith G L and Moss B, *General method for production and selection of infectious vaccinia virus recombinants expressing foreign genes*. J. Virol. (1984) 49: 857-864.

Mann D L, O'Brien S J, Gilbert D A, Reid Y, Popovic M, Read-Connole E, Gallo R C and Gazdar A F, *Origin of the HIV-susceptible human CD4+ cell line H9*. AIDS Res Hum Retroviruses (1989) δ: 253-255.

Mascola J, Louwagie J. McCutchan F E, Fischer C L, Hegerich P A, Wagner K F, Fowler A K, McNeil J G and Burke D S, *Two antigenically distinct subtypes of Human Immunodeficiency Virus Type 1: Viral genotype predicts neutralization serotype*. J Infect Dis. (1994) 169: 48-54.

Mather J P, *Establishment and characterization of two distinct mouse testicular epithelial cell lines*. Biol Reprod. (1980) 23: 243-252.

Mather J P, Zhuang L Z, Perez-Infante V and Phillips D M, *Culture of testicular cells in hormone-supplemented serum-free medium*. Ann NY Acad. Sci. (1982) 383: 44-68.

Merrifield R B, *Automated synthesis of peptides*. Science (1965) 150: 178-185.

Moore J P, Sattentau Q J, Yoshiyama H, Thali M, Charles M, Sullivan N, Poon S-W, Fung M S, Traincard F, Pinkus M, Robey G, Robinson J E, Ho D D and Sodroski J, *Probing the structure of the V2 domain of human immunodeficiency virus type 1 surface glycoprotein gp120 with a panel of eight monoclonal antibodies: human immune response to the V1 and V2 domains*. J. Virol. (1993) 67: 6136-6151.

Montefiori D C, Pantaleo G, Fink L M, Zhou J T, Zhou J Y, Bilska M, Miralles G D and Fauci A S, *Neutralizing and infection-enhancing antibody responses to human immunodeficiency virus type 1 in long-term nonprogressors*. J Infect Dis. (1996) 60-67.

Moore J P, Cao Y, Leu J, Qin L, Korber B and Ho D D. *Inter- and intraclade neutralization of human immunodeficiency virus type 1: genetic clades do not correspond to neutralization serotypes but partially correspond to gp120 antigenic serotypes*. J. Virol. (1996) 70: 427-44.

Muster T, Stein F, Purtscher M, Trkola A, Klima A, Himmier G, Ruker F and Katinger H, *A conserved neutralization epitope on gp41 of human immunodeficiency virus type 1*. J. Virol. (1993) 67: 6642-6647.

Myers E W and Miller W, *Optimal alignments in linear space*. CABIOS (1988) 4: 11-17.

Myers G, Berzofsky J A, Korber B, Smith R F and Paviakis G N, *Human retroviruses and AIDS* 1992. Los Alamos National Laboratory, Los Alamos, N. Mex., 1993.

Overbaugh J and Rudensey L M. *Alterations in potential sites for glycosylatioon predominate during evolution of the simian immunodeficiency virus envelope gene in macaques*. J. Virol. (1992) 66: 5937-5948.

Park E J, Vujcic L J, Anand R, Theodore T S and Quinnan G V, *Mutations in both gp120 and gp41 are responsible for the broad neutralization resistance of variant HIV-1 mn to antibodies directed at v3 and non-v3 epitopes*, J. Virol. (1998) 72: 7099-7107.

Plantier J C, Le Pogam S, Poisson F, Buzelay L, Lejeune B, Barin F, *Extent of antigenic diversity in the V3 region of the surface glycoprotein, gp120, of human immunodeficiency virus type 1 group M and consequences for serotyping*. J. Virol. (1998) 72: 677-83.

Quinnan G, Zhang P, Fu D, Dong M and Margolick J, *Evolution of neutralizing antibody response against hiv-1 virions and pseudovirions in multicenter aids cohort study participants*. AIDS Res Hum Retroviruses (1998) 14: 939-949.

Sabri F, Chiodi F and Fenyo E M, *Lack of correlation between V3 amino acid sequence and syncytium-inducing capacity of some HIV type 1 isolates*. AIDS Res Hum Retroviruses. (1996) 12: 855-858.

Saitou N and Nei M, *The neighbor-joining method: A new method for reconstructing phylogenetic trees*. Mol. Biol. Evol (1987) 4: 406-425.

Schonning K, Jansson B, Olofsson S, Nielsen J O and Hansen J S. *Resistance to V3-directed neutralization caused by an N-linked oligosaccharide depends on the quaternary-structure of the HIV-1 envelope oligomer*. Virol. (1996) 218: 134-140.

Seth A, Hodge D R, Thompson D M, Robinson L, Panayiotakis A, Watson D K and Papas T S, *ETS family proteins activate transcription from HIV-1 long terminal repeat*. AIDS Res Hum Retroviruses (1993) 9: 1017-1023.

Stuve L L, Brown-Shimer S, Pachl C, Naharian R, Diaz D and Burke R L, *Structure and expression of the herpes simplex virus type 2 glycoprotein gB gene*. J. Virol. (1987) 61: 326-335.

Thali M, Charles M, Furman C, Cavacini L, Posner M, Robinson J and Sodroski J, *Resistance to neutralization by broadly reactive antibodies to the human immunodeficiency virus type 1 gp120 glycoprotein conferred by a gp41 amino acid change*. J. Virol. (1994) 68: 674-680.

Thali M, Furman C, Ho D D, Robinson J, Tilley S, Pinter A and Sodroski J, *Discontinuous, conserved neutralization epitopes overlapping the CD4-binding region of human immunodeficiency virus type 1 gp120 envelope glycoprotein*. J. Virol. (1992) 66: 5635-5641.

Thali M, Moore J P, Furman C, Charles M, Ho D D, Robinson J and Sodroski J, *Characterization of conserved human immunodeficiency virus type 1 gp120 neutralization epitopes exposed upon gp120-CD4*. J. Virol. (1993) 67: 3978-3988.

Theodore T S, Englund G, Buckler-White A, Buckler C E, Martin M A and Peden K W, *Construction and characterization of a stable full-length macrophage-tropic HIV tupe 1 molecular clone that directs the production of high titers if progeny virions*. AIDS Res Hum Retroviruses (1996) 12: 191-194.

Trkola A, Purtscher M, Muster T, Ballaun C, Bauchacher A, Sullivan N, Srinivassan K, Sodroski J, Moore J P and Katinger H, *Human monoclonal antibody 2G12 defines a distinctive neutralization epitope of human immunodeficiency virus type 1*. J. Virol. (1996) 70: 1100-1108.

Urlaub G and Chasin L A, *Isolation of Chinese hamster cell mutants deficient in dihydrofolate reductase activity*. Proc Natl Acad Sci USA (1980) 77: 4216-4220.

VanCott T C, Mascola J R, Kaminski R W, Kalyanaraman V, Hallberg P L, Burnett P R, Ulrich J T, Rechtman D J and Birx D L, *Antibodies with specificity to native gp120 and neutralization activity against primary human immunodeficiency virus type 1 isolates elicited by immunization with oligomeric gp160*. J. Virol. (1997) 71: 4319-4330.

Vujcic L K and Quinnan G V, *Preparation and characterization of human HIV type 1 neutralizing reference sera*. (1995) AIDS Res Hum Retroviruses. 11: 783-787.

Wrin T, Loh T P, Vennari J C, Schuitemaker H and Nunberg J H, *Adaptation to persistent growth in the H9 cell line renders a primary isolate of humanimmunodeficiency virus type 1 sensitive to neutralization by vaccine sera*. J. Virol. (1995) 69: 39-48.

Zeng W, Regamey P O, Rose K, Wang Y and Bayer E. *Use of Fmoc-N-(2-hydroxy-4-methoxybenzyl)amino acids in peptide synthesis*. J Pept Res. (1997) 49: 273-279.

Zhang P F, Chen X, Fu D W, Margolick J B and Quinnan G V. *Primary virus envelope cross-reactivity of the broadening neutralizingantibody response during early chronic human-immunodeficiency virus type 1 infection*. J. Virol. (1999) 73: 5225-5230.

Zolla-Pazner S and Sharpe S. *A resting cell assay for improved detection ofantibody-mediated neutralization of HIV type 1 primary isolates*. AIDS Res Hum Retroviruses (1995) 11: 1449-1458.

Zwart G, Langedijk H, Van der Hoek L, de Jong J J, Wolfs T F, Ramautarsing C, Bakker M, De Ronde A and Goudsmit J, *Immunodominance and antigenic variation ofthe principal neutralization domain of HIV-1*. Virol. (1991) 181: 481-489.

---

What is claimed:

1. An isolated nucleic acid molecule encoding an HIV-1 envelope protein comprising SEQ ID NO: 1.

2. An isolated nucleic acid molecule encoding an HIV-1 envelope protein capable of inducing the production of a cross-reactive neutralizing anti-serum against multiple strains of HIV-1 in vitro comprising the amino acid sequence of SEQ ID NO:1.

3. An isolated nucleic acid molecule encoding an HIV-1 envelope protein capable of inducing the production of a cross-reactive neutralizing anti-serum against multiple strains of HIV-1 in vitro wherein the V3 region of the HIV-1 envelope protein comprises SEQ ID NO:3.

4. An isolated nucleic acid molecule which encodes an HIV-1 envelope protein having a V3 region comprising SEQ ID NO:3.

5. The isolated nucleic acid molecule of claim 2, wherein the nucleic acid molecule encodes an HIV-1 envelope protein consisting of SEQ ID NO:1.

6. The isolated nucleic acid molecule of claim 2, wherein said nucleic acid molecule is operably linked to one or more expression control elements.

7. A recombinant vector comprising the nucleic acid molecule of claim 6.

8. The recombinant vector of claim 7, wherein the recombinant vector is a plasmid.

9. The plasmid of claim 8, wherein the plasmid is psV7d env, which has been deposited with ATCC under accession number PTA-7237.

10. The recombinant vector of claim 7, wherein the recombinant vector is an attenuated virus.

11. A composition comprising a recombinant vector of claim 10 and a pharmaceutically acceptable carrier.

12. An isolated host cell line comprising the vector of claim 10.

13. The host cell line of claim 12, wherein the host cell is stably transformed with the vector.

14. The host cell line of claim 12, wherein said host is a prokaryotic host cell.

15. The host cell line of claim 12, wherein said host cell is a eukaryotic host cell.

16. The isolated nucleic acid molecule of claim 3, wherein the HIV-1 envelope protein molecule comprises 50 amino acid residues.

17. The isolated nucleic acid molecule of claim 3, wherein the HIV-1 envelope protein further comprises a C3 region.

18. The isolated nucleic acid molecule of claim 4, wherein the HIV-1 envelope protein further comprises a C3 region.

19. The isolated nucleic acid molecule of claim 3, wherein said nucleic acid molecule is operably linked to one or more expression control elements.

20. A recombinant vector comprising a nucleic acid molecule of claim 19.

21. The recombinant vector of claim 20, wherein the recombinant vector is a plasmid.

22. The recombinant vector of claim 20, wherein the recombinant vector is an attenuated virus.

23. A composition comprising a recombinant vector of claim 20 and a pharmaceutically acceptable carrier.

24. An isolated host cell line comprising the vector of claim 20.

25. The host cell line of claim 24, wherein the host cell is stably transformed with the vector.

26. The host cell line of claim 24, wherein said host is a prokaryotic host cell.

27. The host cell line of claim 24, wherein said host cell is a eukaryotic host cell.

* * * * *

SEQUENCE LISTING

<160> NUMBER OF SEQ ID NOS: 24

<210> SEQ ID NO 1
<211> LENGTH: 866
<212> TYPE: PRT
<213> ORGANISM: Human immunodeficiency virus type 1
<220> FEATURE:
<223> OTHER INFORMATION: R2 strain envelope protein (gp 160)

<400> SEQUENCE: 1

-continued

```
Met Arg Val Lys Gly Ile Arg Arg Asn Tyr Gln His Trp Trp Gly Trp
 1               5                  10                 15

Gly Thr Met Leu Leu Gly Leu Leu Met Ile Cys Ser Ala Thr Glu Lys
            20                  25                 30

Leu Trp Val Thr Val Tyr Tyr Gly Val Pro Val Trp Lys Glu Ala Thr
        35                  40                 45

Thr Thr Leu Phe Cys Ala Ser Asp Ala Lys Ala Tyr Asp Thr Glu Ala
    50                  55                 60

His Asn Val Trp Ala Thr His Ala Cys Val Pro Thr Asp Pro Asn Pro
65                  70                  75                 80

Gln Glu Val Glu Leu Val Asn Val Thr Glu Asn Phe Asn Met Trp Lys
                85                  90                 95

Asn Asn Met Val Glu Gln Met His Glu Asp Ile Ile Ser Leu Trp Asp
            100                 105                110

Gln Ser Leu Lys Pro Cys Val Lys Leu Thr Pro Leu Cys Val Thr Leu
        115                 120                125

Asn Cys Thr Asp Leu Arg Asn Thr Thr Asn Thr Asn Asn Ser Thr Asp
    130                 135                140

Asn Asn Asn Ser Asn Ser Glu Gly Thr Ile Lys Gly Gly Glu Met Lys
145                 150                 155                160

Asn Cys Ser Phe Asn Ile Ala Thr Ser Ile Gly Asp Lys Met Gln Lys
                165                 170                175

Glu Tyr Ala Leu Leu Tyr Lys Leu Asp Ile Glu Pro Ile Asp Asn Asp
            180                 185                190

Asn Thr Ser Tyr Arg Leu Ile Ser Cys Asn Thr Ser Val Ile Thr Gln
        195                 200                205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Lys Lys Phe Ser Gly
225                 230                 235                240

Lys Gly Ser Cys Lys Asn Val Ser Thr Val Gln Cys Thr His Gly Ile
                245                 250                255

Arg Pro Val Val Ser Thr Gln Leu Leu Leu Asn Gly Ser Leu Ala Glu
            260                 265                270

Glu Glu Val Val Ile Arg Ser Glu Asn Phe Thr Asn Asn Ala Lys Thr
        275                 280                285

Ile Ile Val Gln Leu Arg Glu Pro Val Lys Ile Asn Cys Ser Arg Pro
    290                 295                 300

Asn Asn Asn Thr Arg Lys Ser Ile Pro Met Gly Pro Gly Arg Ala Phe
305                 310                 315                320

Tyr Thr Thr Gly Gln Ile Ile Gly Asp Ile Arg Gln Ala His Cys Asn
                325                 330                335

Ile Ser Lys Thr Asn Trp Thr Asn Ala Leu Lys Gln Val Val Glu Lys
            340                 345                350

Leu Gly Glu Gln Phe Asn Lys Thr Lys Ile Val Phe Thr Asn Ser Ser
        355                 360                365

Gly Gly Asp Pro Glu Ile Val Thr His Ser Phe Asn Cys Ala Gly Glu
    370                 375                 380

Phe Phe Tyr Cys Asn Thr Thr Gln Leu Phe Asp Ser Ile Trp Asn Ser
385                 390                 395                400

Glu Asn Gly Thr Trp Asn Ile Thr Arg Gly Leu Asn Asn Thr Gly Arg
                405                 410                415

Asn Asp Thr Ile Thr Leu Pro Cys Arg Ile Lys Gln Ile Ile Asn Arg
```

-continued

```
                420                 425                 430
Trp Gln Glu Val Gly Lys Ala Met Tyr Ala Pro Pro Ile Lys Gly Asn
                435                 440                 445
Ile Ser Cys Ser Ser Asn Ile Thr Gly Leu Leu Leu Thr Arg Asp Gly
450                 455                 460
Gly Lys Asp Asp Asn Ser Arg Asp Gly Asn Glu Thr Phe Arg Pro Gly
465                 470                 475                 480
Gly Gly Asp Met Arg Asp Asn Trp Arg Ser Glu Leu Tyr Lys Tyr Lys
                485                 490                 495
Val Val Lys Ile Glu Pro Leu Gly Val Ala Pro Thr Lys Ala Lys Arg
                500                 505                 510
Arg Val Val Gln Arg Glu Glu Arg Ala Val Gly Leu Gly Ala Met Phe
                515                 520                 525
Phe Gly Phe Leu Gly Ala Ala Gly Ser Thr Met Gly Ala Ala Ser Val
                530                 535                 540
Thr Leu Thr Val Gln Ala Arg Gln Leu Leu Ser Gly Ile Val Gln Gln
545                 550                 555                 560
Gln Ser Asn Leu Leu Arg Ala Ile Glu Ala Gln Gln His Leu Leu Gln
                565                 570                 575
Leu Thr Val Trp Gly Ile Lys Gln Leu Gln Ala Arg Ile Leu Ala Val
                580                 585                 590
Glu Arg Tyr Leu Lys Asp Gln Gln Leu Leu Gly Ile Trp Gly Cys Ser
                595                 600                 605
Gly Lys Leu Ile Cys Thr Thr Thr Val Pro Trp Asn Ala Ser Trp Ser
610                 615                 620
Lys Asn Lys Thr Leu Glu Ala Ile Trp Asn Asn Met Thr Trp Met Gln
625                 630                 635                 640
Trp Asp Lys Glu Ile Asp Asn Tyr Thr Ser Leu Ile Tyr Ser Leu Ile
                645                 650                 655
Glu Glu Ser Pro Ile Gln Gln Glu Lys Asn Glu Gln Glu Leu Leu Glu
                660                 665                 670
Leu Asp Lys Trp Ala Asn Leu Trp Asn Trp Phe Asp Ile Ser Asn Trp
                675                 680                 685
Leu Trp Tyr Ile Lys Ile Phe Ile Met Ile Val Gly Gly Leu Val Gly
                690                 695                 700
Leu Arg Ile Val Phe Val Val Leu Ser Ile Val Asn Arg Val Arg Gln
705                 710                 715                 720
Gly Tyr Ser Pro Leu Ser Phe Gln Thr Arg Leu Pro Ala Pro Arg Gly
                725                 730                 735
Pro Asp Arg Pro Glu Glu Ile Glu Glu Glu Gly Gly Asp Arg Asp Arg
                740                 745                 750
Asp Arg Ser Gly Leu Leu Val Asp Gly Phe Leu Thr Leu Ile Trp Val
                755                 760                 765
Asp Leu Arg Ser Leu Cys Leu Phe Ser Tyr His Arg Leu Arg Asp Leu
                770                 775                 780
Leu Leu Ile Val Thr Arg Ile Val Glu Leu Leu Gly Arg Arg Gly Trp
785                 790                 795                 800
Glu Ile Leu Lys Tyr Trp Trp Asn Leu Leu Gln Tyr Trp Ser Gln Glu
                805                 810                 815
Leu Lys Asn Ser Ala Val Ser Leu Phe Asn Ala Thr Ala Ile Ala Val
                820                 825                 830
Ala Glu Gly Thr Asp Arg Val Ile Gln Val Leu Gln Arg Val Gly Arg
                835                 840                 845
```

-continued

```
Ala Leu Leu His Ile Pro Thr Arg Ile Arg Gln Gly Leu Glu Arg Ala
    850                 855                 860

Leu Leu
865

<210> SEQ ID NO 2
<211> LENGTH: 17
<212> TYPE: PRT
<213> ORGANISM: Human immunodeficiency virus type 1
<220> FEATURE:
<223> OTHER INFORMATION: segment of R2 strain V3 domain

<400> SEQUENCE: 2

Lys Ser Ile Pro Met Gly Pro Gly Arg Ala Phe Tyr Thr Thr Gly Gln
  1               5                  10                  15

Ile

<210> SEQ ID NO 3
<211> LENGTH: 35
<212> TYPE: PRT
<213> ORGANISM: Human immunodeficiency virus type 1
<220> FEATURE:
<223> OTHER INFORMATION: R2 strain V3 domain

<400> SEQUENCE: 3

Cys Ser Arg Pro Asn Asn Asn Thr Arg Lys Ser Ile Pro Met Gly Pro
  1               5                  10                  15

Gly Arg Ala Phe Tyr Thr Thr Gly Gln Ile Ile Gly Asp Ile Arg Gln
             20                  25                  30

Ala His Cys
         35

<210> SEQ ID NO 4
<211> LENGTH: 35
<212> TYPE: PRT
<213> ORGANISM: Human immunodeficiency virus type 1
<220> FEATURE:
<223> OTHER INFORMATION: V3 domain of strain 93TH966.8

<400> SEQUENCE: 4

Cys Thr Arg Pro Ser Asn Asn Thr Arg Thr Ser Thr Thr Ile Gly Pro
  1               5                  10                  15

Gly Gln Val Phe Tyr Arg Thr Gly Asp Ile Thr Gly Asn Ile Arg Lys
             20                  25                  30

Ala Tyr Cys
         35

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: derivatives
      of segment of V3 domain in R2 strain
<220> FEATURE:
<221> NAME/KEY: VARIANT
<222> LOCATION: (3)..(12)
<223> OTHER INFORMATION: X = any natural or non-natural amino acid.

<400> SEQUENCE: 5

Pro Met Xaa Xaa Xaa Xaa Xaa Xaa Xaa Xaa Xaa Xaa Gln
  1               5                  10
```

<210> SEQ ID NO 6
<211> LENGTH: 30
<212> TYPE: PRT
<213> ORGANISM: Human immunodeficiency virus type 1
<220> FEATURE:
<223> OTHER INFORMATION: sequence of Phenetic 1 in V3 region

<400> SEQUENCE: 6

Asn Asn Thr Arg Lys Ser Ile His Ile Gly Pro Gly Arg Ala Phe Tyr
 1               5                  10                  15

Thr Thr Gly Asp Ile Ile Gly Asp Ile Arg Gln Ala His Cys
            20                  25                  30

<210> SEQ ID NO 7
<211> LENGTH: 30
<212> TYPE: PRT
<213> ORGANISM: Human immunodeficiency virus type 1
<220> FEATURE:
<223> OTHER INFORMATION: sequence of Phenetic 2 in V3 region

<400> SEQUENCE: 7

Asn Asn Thr Arg Lys Ser Ile Ser Ile Gly Pro Gly Arg Ala Phe Tyr
 1               5                  10                  15

Ala Thr Gly Glu Ile Ile Gly Asp Ile Arg Gln Ala His Cys
            20                  25                  30

<210> SEQ ID NO 8
<211> LENGTH: 30
<212> TYPE: PRT
<213> ORGANISM: Human immunodeficiency virus type 1
<220> FEATURE:
<223> OTHER INFORMATION: sequence of Phenetic 3 in V3 region

<400> SEQUENCE: 8

Asn Asn Thr Arg Lys Ser Ile Ser Ile Gly Pro Gly Arg Ala Phe Tyr
 1               5                  10                  15

Ala Thr Gly Lys Ile Ile Gly Asp Ile Arg Gln Ala His Cys
            20                  25                  30

<210> SEQ ID NO 9
<211> LENGTH: 30
<212> TYPE: PRT
<213> ORGANISM: Human immunodeficiency virus type 1
<220> FEATURE:
<223> OTHER INFORMATION: sequence of Phenetic 4 in V3 region

<400> SEQUENCE: 9

Asn Asn Thr Arg Lys Ser Ile Arg Ile Gly Pro Gly Gln Ala Phe Tyr
 1               5                  10                  15

Ala Thr Gly Asp Ile Ile Gly Asp Ile Arg Gln Ala His Cys
            20                  25                  30

<210> SEQ ID NO 10
<211> LENGTH: 30
<212> TYPE: PRT
<213> ORGANISM: Human immunodeficiency virus type 1
<220> FEATURE:
<223> OTHER INFORMATION: sequence of Phenetic 5 in V3 region

<400> SEQUENCE: 10

Asn Asn Thr Arg Lys Ser Ile His Ile Gly Pro Gly Arg Ala Phe Tyr
 1               5                  10                  15

Ala Thr Gly Lys Ile Ile Gly Asp Ile Arg Gln Ala His Cys
            20                  25                  30

```
<210> SEQ ID NO 11
<211> LENGTH: 30
<212> TYPE: PRT
<213> ORGANISM: Human immunodeficiency virus type 1
<220> FEATURE:
<223> OTHER INFORMATION: sequence of Phenetic 6 in V3 region

<400> SEQUENCE: 11

Lys Asn Thr Arg Arg Ser His Ile Gly Pro Gly Arg Ala Phe Tyr
 1               5                  10                  15

Thr Thr Lys Gln Ile Ile Gly Asp Ile Arg Gln Ala His Cys
            20                  25                  30

<210> SEQ ID NO 12
<211> LENGTH: 30
<212> TYPE: PRT
<213> ORGANISM: Human immunodeficiency virus
<220> FEATURE:
<223> OTHER INFORMATION: sequence of Phenetic 7 in V3 region

<400> SEQUENCE: 12

Asn Asn Thr Arg Thr Ser Ile Thr Ile Gly Pro Gly Gln Val Phe Tyr
 1               5                  10                  15

Arg Thr Gly Lys Ile Ile Gly Asp Ile Arg Gln Ala His Cys
            20                  25                  30

<210> SEQ ID NO 13
<211> LENGTH: 30
<212> TYPE: PRT
<213> ORGANISM: Human immunodeficiency virus type 1
<220> FEATURE:
<223> OTHER INFORMATION: sequence of Phenetic 8 in V3 region

<400> SEQUENCE: 13

Lys Lys Met Arg Thr Ser Ala Arg Ile Gly Pro Gly Arg Val Phe His
 1               5                  10                  15

Lys Thr Gly Asp Ile Ile Gly Ser Ile Thr Lys Ala Tyr Cys
            20                  25                  30

<210> SEQ ID NO 14
<211> LENGTH: 29
<212> TYPE: PRT
<213> ORGANISM: Human immunodeficiency virus type 1
<220> FEATURE:
<223> OTHER INFORMATION: sequence of Phenetic 9 in V3 region

<400> SEQUENCE: 14

Asn Asn Thr Arg Gln Ser Thr His Ile Gly Pro Gly Gln Ala Leu Tyr
 1               5                  10                  15

Thr Thr Asp Ile Ile Gly Lys Ile Arg Gln Ala His Cys
            20                  25

<210> SEQ ID NO 15
<211> LENGTH: 29
<212> TYPE: PRT
<213> ORGANISM: Human immunodeficiency virus type 1
<220> FEATURE:
<223> OTHER INFORMATION: sequence of Phenetic 10 in V3 region

<400> SEQUENCE: 15

Asn Asn Thr Arg Gln Gly Thr His Ile Gly Pro Gly Arg Ala Tyr Tyr
 1               5                  10                  15

Thr Thr Asn Ile Ile Gly Asp Ile Arg Gln Ala His Cys
            20                  25
```

<210> SEQ ID NO 16
<211> LENGTH: 29
<212> TYPE: PRT
<213> ORGANISM: Human immunodeficiency virus
<220> FEATURE:
<223> OTHER INFORMATION: sequence of Phenetic 11 in V3 region

<400> SEQUENCE: 16

Asn Asn Thr Arg Gln Arg Thr Ser Ile Gly Gln Gly Gln Ala Leu Tyr
 1               5                  10                  15

Thr Thr Glu Ile Arg Gly Asp Ile Arg Gln Ala Ala Cys
            20                  25

<210> SEQ ID NO 17
<211> LENGTH: 30
<212> TYPE: PRT
<213> ORGANISM: Human immunodeficiency virus type 1
<220> FEATURE:
<223> OTHER INFORMATION: sequence of Phenetic 12 in V3 region

<400> SEQUENCE: 17

Asp Asn Ile Lys Ile Gln Arg Thr Pro Ile Gly Gln Gly Gln Ala Leu
 1               5                  10                  15

Tyr Thr Thr Arg Ile Thr Gly Tyr Ile Gly Gln Ala His Cys
            20                  25                  30

<210> SEQ ID NO 18
<211> LENGTH: 29
<212> TYPE: PRT
<213> ORGANISM: Human immunodeficiency virus type 1
<220> FEATURE:
<223> OTHER INFORMATION: sequence of Phenetic 13 in V3 region

<400> SEQUENCE: 18

Gln Asn Lys Arg Gln Gly Thr Pro Ile Gly Leu Gly Gln Ala Leu Tyr
 1               5                  10                  15

Thr Thr Arg Ile Lys Gly Asp Ile Arg Lys Ala His Cys
            20                  25

<210> SEQ ID NO 19
<211> LENGTH: 30
<212> TYPE: PRT
<213> ORGANISM: Human immunodeficiency virus type 1
<220> FEATURE:
<223> OTHER INFORMATION: sequence of Clade A in V3 region

<400> SEQUENCE: 19

Asn Asn Thr Arg Lys Ser Val His Ile Gly Pro Gly Gln Ala Phe Tyr
 1               5                  10                  15

Ala Thr Gly Asp Ile Ile Gly Asp Ile Arg Gln Ala His Cys
            20                  25                  30

<210> SEQ ID NO 20
<211> LENGTH: 30
<212> TYPE: PRT
<213> ORGANISM: Human immunodeficiency virus type 1
<220> FEATURE:
<223> OTHER INFORMATION: sequence of Clade B in V3 region

<400> SEQUENCE: 20

Asn Asn Thr Arg Lys Ser Ile His Ile Gly Pro Gly Arg Ala Phe Tyr
 1               5                  10                  15

Thr Thr Gly Glu Ile Ile Gly Asp Ile Arg Gln Ala His Cys

-continued

```
                        20                  25                  30
```

<210> SEQ ID NO 21
<211> LENGTH: 30
<212> TYPE: PRT
<213> ORGANISM: Human immunodeficiency virus type 1
<220> FEATURE:
<223> OTHER INFORMATION: sequence of Clade C in V3 region

<400> SEQUENCE: 21

Asn Asn Thr Arg Lys Ser Ile Arg Ile Gly Pro Gly Gln Thr Phe Tyr
  1               5                  10                  15

Ala Thr Gly Asp Ile Ile Gly Asp Ile Arg Gln Ala His Cys
             20                  25                  30

<210> SEQ ID NO 22
<211> LENGTH: 29
<212> TYPE: PRT
<213> ORGANISM: Human immunodeficiency virus type 1
<220> FEATURE:
<223> OTHER INFORMATION: sequence of Clade D in V3 region

<400> SEQUENCE: 22

Asn Asn Thr Arg Gln Arg Thr His Ile Gly Pro Gly Gln Ala Leu Tyr
  1               5                  10                  15

Thr Thr Arg Ile Ile Gly Asp Ile Arg Gln Ala His Cys
             20                  25

<210> SEQ ID NO 23
<211> LENGTH: 30
<212> TYPE: PRT
<213> ORGANISM: Human immunodeficiency virus type 1
<220> FEATURE:
<223> OTHER INFORMATION: sequence of Clade E in V3 region

<400> SEQUENCE: 23

Asn Asn Thr Arg Thr Ser Ile Thr Ile Gly Pro Gly Gln Val Phe Tyr
  1               5                  10                  15

Arg Thr Gly Asp Ile Ile Gly Asp Ile Arg Lys Ala Tyr Cys
             20                  25                  30

<210> SEQ ID NO 24
<211> LENGTH: 2601
<212> TYPE: DNA
<213> ORGANISM: Human immunodeficiency virus type 1

<400> SEQUENCE: 24
atgagagtga aggggatcag gaggaattat cagcactggt ggggatgggg cacgatgctc    60
cttgggttat taatgatctg tagtgctaca gaaaaattgt gggtcacagt ctattatggg   120
gtacctgtgt ggaaagaagc aaccaccact ctattttgtg catcagatgc aaagcatat    180
gatacagagg cacataatgt ttgggccaca catgcctgtg tacccacaga ccccaaccca   240
caagaagtag aattggtaaa tgtgacagaa aattttaaca tgtggaaaaa taacatggta   300
gaacagatgc atgaggatat aatcagttta tgggatcaaa gcctaaagcc atgcgtaaaa   360
ttaaccccac tctgtgttac tttaaattgc actgatttga ggaatactac taataccaat   420
aatagtactg ataataacaa tagtaatagc gaggaacaa taagggagg agaaatgaaa    480
aactgctctt tcaatatcgc cacaagcata ggagataaga tgcagaaaga atatgcactt   540
ctttataaac ttgatataga accaatagat aatgataata ccagctatag gttgataagt   600
tgtaatacct cagtcattac acaagcttgt ccaaagatat cctttgagcc aattcccata   660
```

```
cactattgtg ccccggctgg ttttgcgatt ctaaagtgta acgataaaaa gttcagtgga    720
aaaggatcat gtaaaaatgt cagcacagta caatgtacac atggaattag gccagtagta    780
tcaactcaac tgctgttaaa tggcagtcta gcagaagaag aggtagtaat tagatctgag    840
aatttcacaa acaatgctaa aaccataata gtacagctga gagaacctgt aaaaattaat    900
tgttcaagac ccaacaacaa tacaagaaaa agtatacota tgggaccagg gagagcattt    960
tatacaacag gacaaataat aggagatata agacaagcac attgtaatat tagtaaaaca   1020
aattggacta acgctttaaa acaggtagtt gaaaaactag gggaacaatt caacaagaca   1080
aaaatagtct ttacgaactc ctcaggaggg gacccagaaa ttgtaacgca cagttttaat   1140
tgtgcagggg aattttctcta ctgtaataca acacaactgt ttgatagtat ttggaatagt   1200
gagaatggta cttggaatat tactaggggg ttaaataaca ctggaagaaa tgacacaatc   1260
acactcccat gcaggataaa acaaattata aacaggtggc aggaagtagg aaaagcaatg   1320
tatgcccctc ccatcaaagg aaacattagc tgttcatcaa atattacagg gctgctatta   1380
acaagagatg gtggtaagga tgataatagc agggacggga acgagacctt cagacctgga   1440
ggaggagata tgagggacaa ttggagaagt gaattatata aatataaagt agtaaaaatt   1500
gaaccattag gagtagcacc caccaaggca agagaagag tggtgcaaag agaagaaaga   1560
gcagtgggac taggagctat gttcattggg ttcttgggag cagcaggaag cactatgggc   1620
gcagcgtcag tgacgctgac ggtacaggcc aggcaattat tgtctggtat agtgcaacag   1680
cagagcaatt tgctgagagc tattgaggcg caacagcatc tgttgcaact cacagtctgg   1740
ggcatcaagc agctccaggc aagaatcctg gctgtggaaa gatacctaaa ggatcaacag   1800
ctcctaggga tttggggttg ctctggaaaa ctcatttgca ccactactgt gccttggaat   1860
gctagttgga gtaagaataa aactctggaa gctatttgga ataacatgac ctggatgcag   1920
tgggacaaag agattgacaa ttacacaagc ttaatatact ccttaattga agaatcgcag   1980
atccaacaag aaaagaatga acaagaatta ttggaattag ataaatgggc aaatctgtgg   2040
aattggtttg acatatcaaa ctggctgtgg tatataaaaa tattcataat gatagtagga   2100
ggcttggtag gtttaaggat agtttttgtt gtactttcta tagtgaatag agttaggcag   2160
ggatactcac cattatcgtt tcagacccgc ctcccagccc cgaggggacc cgacaggccc   2220
gaagaaatcg aagaagaagg tggagacaga gacagagaca gatccgggct cttagtggat   2280
ggattcttaa cacttatctg ggtcgacctg cggagcctgt gcctcttcag ctaccaccgc   2340
ttgagagact tactcttgat tgtgacgagg attgtggaac ttctgggacg caggggggtgg   2400 gaaatcctca aatattggtg gaatctcctg cagtattgga gtcaggaact aaagaatagt   2460
gctgttagct tgttcaacgc caccgccata gcagtagctg agggaacaga tagggttata   2520
gaagtattac aaagagttgg tagagctttg ctccacatac ctacaagaat aagacagggc   2580
ttggaaaggg ctttgctata a                                             2601
```